US011198127B2

(12) United States Patent
Sulchek et al.

(10) Patent No.: US 11,198,127 B2
(45) Date of Patent: Dec. 14, 2021

(54) METHODS FOR CONVECTIVELY-DRIVEN INTRACELLULAR DELIVERY

(71) Applicant: Georgia Tech Research Corporation, Atlanta, GA (US)

(72) Inventors: Todd Sulchek, Atlanta, GA (US); Alexander Alexeev, Atlanta, GA (US); Anna Liu, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 363 days.

(21) Appl. No.: 16/348,170

(22) PCT Filed: Nov. 8, 2017

(86) PCT No.: PCT/US2017/060644
§ 371 (c)(1),
(2) Date: May 8, 2019

(87) PCT Pub. No.: WO2018/089497
PCT Pub. Date: May 17, 2018

(65) Prior Publication Data
US 2019/0262835 A1    Aug. 29, 2019

Related U.S. Application Data

(60) Provisional application No. 62/419,041, filed on Nov. 8, 2016.

(51) Int. Cl.
*B01L 3/00* (2006.01)
*C12M 3/06* (2006.01)
(Continued)

(52) U.S. Cl.
CPC ....... *B01L 3/502761* (2013.01); *C12M 23/16* (2013.01); *C12M 35/04* (2013.01);
(Continued)

(58) Field of Classification Search
CPC .......... B01L 3/502761; B01L 2300/08; B01L 2300/123; B01L 2400/0463;
(Continued)

(56) References Cited

U.S. PATENT DOCUMENTS

2013/0345729 A1    12/2013  Li et al.
2014/0227777 A1    8/2014   Choi et al.
(Continued)

FOREIGN PATENT DOCUMENTS

WO    2016/070136    5/2016
WO    2017/083391    5/2017

OTHER PUBLICATIONS

Lincoln et al. Deformability-Based Flow Cytometry. Cytometry Part A (2004), 59A, 203-209 (Year: 2004).*
(Continued)

*Primary Examiner* — Sean C. Barron
(74) *Attorney, Agent, or Firm* — Troutman Pepper Hamilton Sanders LLP; Ryan A. Schneider

(57) ABSTRACT

Embodiments of the present disclosure can include a method for convective intracellular delivery including providing cells and molecules to a microchannel having compressive surfaces, wherein the compressive surfaces define compression gaps having a height of from 20 and 80% of the average cell diameter; and a plurality of relaxation spaces disposed between the compressive surfaces; flowing the cell medium through the microchannel, wherein as the cell medium flows through the microchannel, the plurality of cells undergo a convective intracellular delivery process comprising: compressing the plurality of cells, wherein the compressing causes the plurality of cells to undergo a loss in intracellular volume ($V_{loss}$); and passing the plurality of cells to a first
(Continued)

relaxation space, wherein the plurality of cells undergo a gain in volume ($V_{gain}$) and absorb a portion of the plurality of molecules.

20 Claims, 24 Drawing Sheets

(51) Int. Cl.
*C12M 1/42* (2006.01)
*C12M 1/00* (2006.01)
*C12N 15/87* (2006.01)
*C12N 5/07* (2010.01)

(52) U.S. Cl.
CPC ............ *C12M 47/04* (2013.01); *C12M 99/00* (2013.01); *C12N 15/87* (2013.01); *B01L 2300/08* (2013.01); *B01L 2300/123* (2013.01); *B01L 2400/0463* (2013.01); *B01L 2400/0487* (2013.01); *B01L 2400/086* (2013.01); *C12N 5/06* (2013.01)

(58) Field of Classification Search
CPC ...... B01L 2400/0487; B01L 2400/086; C12M 99/00; C12M 23/16; C12M 35/04; C12M 47/04; C12N 15/87; C12N 5/06
See application file for complete search history.

(56) References Cited

U.S. PATENT DOCUMENTS

2014/0287509 A1\* 9/2014 Sharei ................... C12M 35/02
435/455
2016/0193605 A1 7/2016 Sharei et al.

OTHER PUBLICATIONS

Search Report from European Application No. 17868899.0 dated Jun. 2, 2020 (9 pages).
Sharei, et al., "A Vector-Free Microfluidic Platform for Intracellular Delivery," Proceedings of the National Academy of Sciences, Jan. 22, 2013, vol. 10, No. 6 pp. 2082-2087.
Wang, et al., "Microfluidic Cellular Enrichment and Separation Through Differences in Viscoelastic Deformation," Lab on a Chip, Jan. 1, 2015, vol. 15, No. 2, pp. 523-540.
Li, et al., "Microfluidic-Enabled Intracellular Delivery of Membrane Impermeable Inhibitors to Study Target Engagement in Human Primary Cells," ACS Chemical Biology, Dec. 15, 2017, vol. 12, No. 12, pp. 2970-2974.
International Search Report and Written Opinion from application PCT/US2017/060644 dated Feb. 15, 2018 (16 pages).

\* cited by examiner

METHODS FOR CONVECTIVELY-DRIVEN INTRACELLULAR DELIVERY

CROSS-REFERENCE TO RELATED APPLICATIONS

This application, filed Nov. 8, 2017, claims the benefit of U.S. Provisional Patent Application Ser. No. 62/419,041, filed Nov. 8, 2016, entitled "Ridged Microchannels for Compressing and Opening Pores Into cells for Molecular and Particle Delivery," the entire contents and substance of which are hereby incorporated by reference as if fully set forth below.

STATEMENT OF FEDERALLY SPONSORED RESEARCH

This invention was made with Government support under Grant Number DGE-1650044 awarded by the National Science Foundation and Grant Number IR21CA191243-01A1 awarded by the NIH. The Government has certain rights in the invention.

BACKGROUND

Intracellular molecular delivery is important in cell manufacturing applications, especially gene transfection and editing. Known methods of intracellular molecular delivery result in very low delivery efficiencies for very large macromolecules (>500 kDa) to the cells, and also precludes delivery to the cell nucleus. Additionally, these methods result in device clogging that decrease the throughput capabilities of such devices Cells can substantially change their shape without changing volume. Cell manipulations due to significant deformations of up to 85% strain applied across a range of timescales from ~10 µs to >1s have described cell deformation and shape change but have not described cell volume change.

BRIEF SUMMARY

Embodiments of the present disclosure can include a method for convective intracellular delivery, the method comprising providing a cell medium and a plurality of molecules to a microchannel, the cell medium comprising a plurality of cells and the microchannel comprising: a first wall and a second wall, the walls being substantially planar to each other and the first wall having a plurality of compressive surfaces, wherein each compressive surface protrudes outwardly from the first wall and defines a compression gap between the compressive surface and the second wall, wherein the compression gap has a height of between 20 and 80% of the average cell diameter; and a plurality of relaxation spaces disposed between the compressive surfaces; flowing the cell medium through the microchannel at a flow velocity, wherein as the cell medium flows through the microchannel, the plurality of cells undergo a convective intracellular delivery process comprising: compressing the plurality of cells in a first compression gap, wherein the compressing causes the plurality of cells to undergo a loss in intracellular volume ($V_{loss}$); and passing the plurality of cells to a first relaxation space, wherein the plurality of cells undergo a gain in volume ($V_{gain}$) and absorb a portion of the plurality of molecules; and collecting the plurality of cells in an outlet.

Embodiments of the present disclosure can include a method for intracellular delivery comprising: applying a plurality of cells and a plurality of molecules to a microchannel, the microchannel having: a first orthogonal surface defining a first compression gap; a second orthogonal surface defining a second compression gap; and a relaxation space disposed between the first and second orthogonal surfaces; flowing the plurality of cells to the microchannel at a flow velocity of 100 to 500 mm/s; applying at the first orthogonal surface a compressive force to the cells, wherein the compressive force causes the cells to undergo a first loss in volume ($V_{loss1}$); passing the plurality of cells through a first relaxation space, wherein the plurality of cells undergo a first gain in volume ($V_{gain1}$); applying at the second orthogonal surface a compressive force to the cells, wherein the compressive force causes the cells to undergo a second loss in volume ($V_{loss2}$); and collecting the plurality of cells at a collection point, wherein as the plurality of cells are collected they undergo a second gain in volume ($V_{gain2}$), wherein as the plurality of cells undergo at least one of $V_{gain1}$ and $V_{gain2}$ they absorb a portion of the plurality of molecules.

Embodiments of the present disclosure can include a system for intracellular delivery comprising: a microchannel comprising: a first wall and a second wall, the walls being substantially planar to each other and the first wall having a plurality of compressive surfaces, wherein each compressive surface protrudes outwardly to the first wall and defines a compression gap between the compressive surface and a surface of the second wall, and a plurality of relaxation spaces disposed between the compressive surfaces; and a cell medium comprising a plurality of cells and a plurality of molecules, the cell medium flowing through the microchannel at a flow velocity, wherein as the cell medium flows through the microchannel, the plurality of cells undergo a convective intracellular delivery process comprising: compressing the plurality of cells in a first compression gap, wherein the compressing causes the cells to undergo a loss in volume ($V_{loss}$); passing the plurality of cells to a first relaxation space, wherein the plurality of cells undergo a gain in volume ($V_{gain}$) and absorb a portion of the plurality of molecules; and wherein the compression gap has a height of from 20 to 80% of the average cell diameter.

Embodiments of the present disclosure can include a cell comprising a plurality of macromolecules having an average diameter of 3 kDa to 6 MDa the cell formed by a process comprising: providing a cell medium and a plurality of molecules to a microchannel, the cell medium comprising the cell and the microchannel comprising: a first wall and a second wall, the walls being substantially planar to each other and the first wall having a plurality of compressive surfaces wherein each compressive surface protrudes normal to the first wall and defines a compression gap between the compressive surface and the second wall, wherein the compression gap has a height of from 20 to 80% of the cell diameter, and a plurality of relaxation spaces disposed between the compressive surfaces; flowing the cell medium through the microchannel at a flow velocity, wherein as the cell medium flows through the microchannel, the cell undergoes a convective intracellular delivery process comprising: compressing the cell in a first compression gap, wherein the compressing causes the cell to undergo a loss in volume ($V_{loss}$); passing the cell to a first relaxation space, wherein the cell undergoes a gain in volume ($V_{gain}$) and absorbs a portion of the plurality of molecules; and collecting the cell in an outlet.

In some embodiments, the compressive surface(s) of any of the above-described systems or methods can comprise a plurality of ridges that are diagonally oriented with respect to a central flow axis of the microchannel. In some embodiments, an angle formed by a ridge can be 30 degrees with respect to the central axis of the microchannel. In other embodiments. In other embodiments, an angle formed by a ridge can be 45 degrees with respect to the central axis of the microchannel. In other embodiments, an angle formed by the ridge can be from 20 to 90 degrees with respect to the central axis of the microchannel. In some embodiments of any of the above-described systems or methods, the microchannel can include a plurality of ridges and the plurality of ridges can be arranged in a chevron pattern within the microchannel. In some embodiments, the plurality of compressive surfaces can comprise from 1 to 21 ridges. In other embodiments, the plurality of compressive surfaces can comprise from 1 to 7 ridges.

In some embodiments, the molecules of any of the above-described systems or methods, can include at least one of macromolecules, nanoparticles, dextran, plasmids, mRNA, antibodies, beads, or viruses. In some embodiments, the macromolecules can have an average size of from 3 kDa to 6 MDa.

In some embodiments, the microchannel of any of the above-described systems or methods, can include at least one inlet. In some embodiments, the plurality of relaxation spaces of any of the above-described systems or methods, can be from 100 to 300 microns. In some embodiments, the plurality of compressive surfaces of any of the above-described systems or methods, can be substantially orthogonal. In some embodiments, the plurality of compression gaps can be from 20 to 80% an average cell diameter.

In some embodiments, the flow velocity of any of the above-described systems or methods, can be from 100 to 500 mm/sec.

In some embodiments, the $V_{loss}$ of any of the above-described systems or methods can be from 5% to 30% the average cell volume. In other embodiments, $V_{loss}$ can be 25% the average cell volume. In some embodiments, the $V_{loss}$ of any of the above-described systems or methods can occur in about 10 μs measured from when the cell first encounters a compressive surface. In some embodiments, the $V_{gain}$ of any of the above-described systems or methods can be 25% to 100% $V_{loss}$. In some embodiments, $V_{gain}$ of approximately 100% $V_{loss}$ can occur in from 4 to 100 ms.

DETAILED DESCRIPTION

Figure 1A:
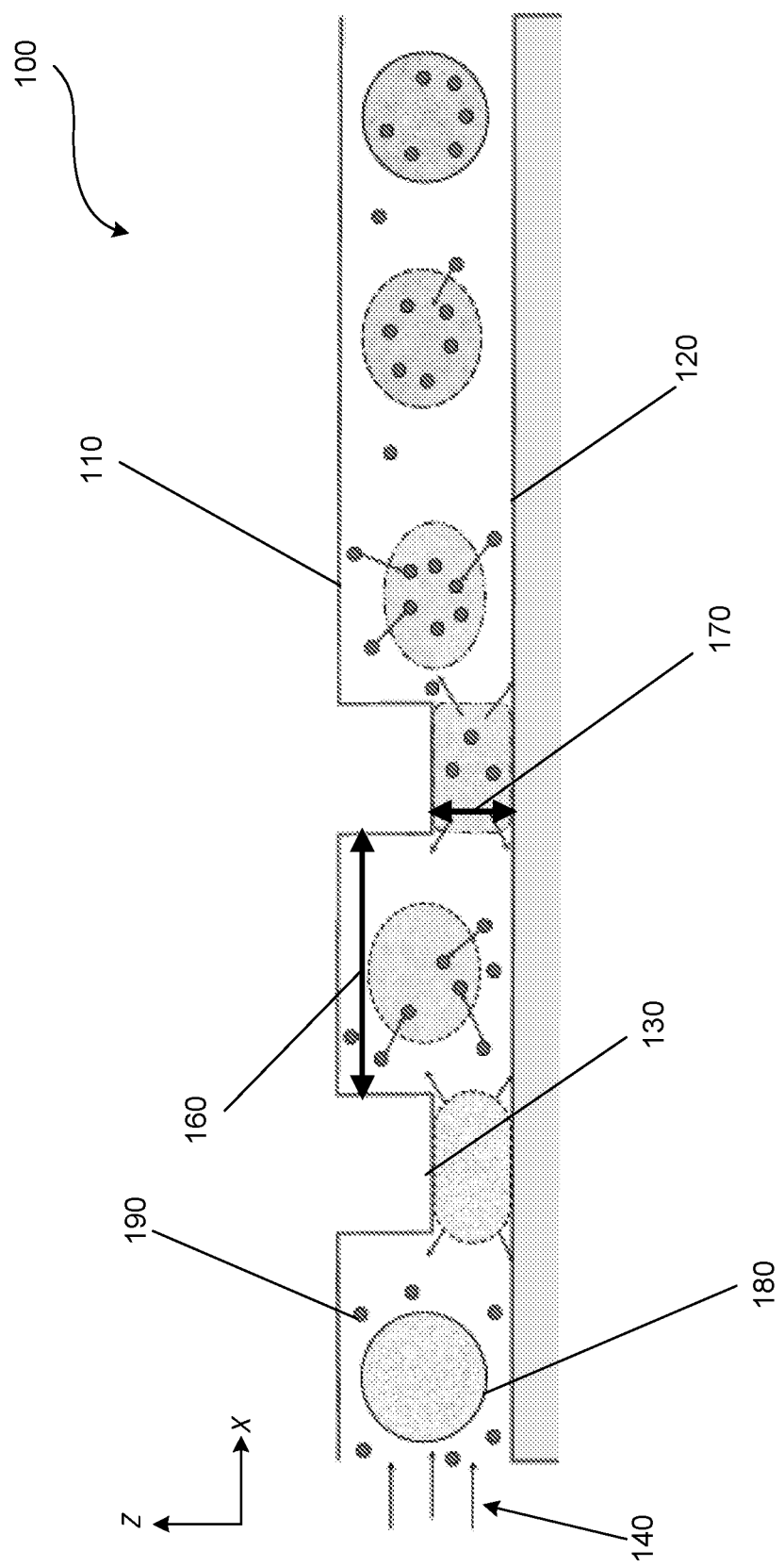
FIG. 1a shows a cross-sectional view of a cell undergoing compression under compressive surfaces, in accordance with one or more embodiments of the present disclosure.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Embodiments of the present disclosure can achieve a cell behavior of transient (up to 30%) cell volume change in response to large magnitude deformations at ultrafast timescales without impairing cell viability. Known methods for intracellular delivery of molecules and/or particles to cells rely on diffusive delivery of molecules and/or particles to cells, which does not rely on cell volume change. Instead, such diffusive delivery uses shear and/or compressive forces to create micro-pores in the cell membrane. The cell membrane is susceptible to manipulation for intracellular delivery, yet in order to maintain high cell viability and avoid cell damage or death, such manipulation is limited in both scale (e.g. amount of force, size of pores, and number of compressions) and the types of molecules that can be delivered (e.g. smaller molecule delivery, not macromolecule delivery above a few hundred kiloDalton). Additionally, absent an external concentration difference between inside and outside the cell, diffusion will not occur in a way to facilitate intracellular delivery. A mechanism for obtaining volume flow and corresponding "convective" volume reuptake is not described. In fact, it is expected in the art and that forcing substantial volume (such as liquids within the cell, e.g. cell cytoplasm) out of a cell is not possible without substantial cell damage and cell death. Surprisingly, embodiments of the present disclosure can achieve bulk volume transfer in substantial amounts, which can facilitate improved intracellular molecular deliver with high cell viability.

Additionally, known microfluidic devices for obtaining diffusive delivery are prone to clogging, due to the need to use narrow constrictions in order to operate at high shear to facilitate cell membrane pore creation and obtain diffusive delivery. Attempts to reduce cell clogging by using high shear force combined with high flow rate, can result in cell damage and cell death. Also, repeated exposure to high shear force can result in cell damage and cell death.

Embodiments of the present disclosure can obtain abrupt volume decrease and fluid transfer during recover results in high-throughput delivery of a variety of macromolecules with high cell viability. Additionally, embodiments of the present disclosure can be used to deliver a variety of macromolecules to a variety of different cell types. Embodiments of the present disclosure have the benefit of providing higher throughput delivery with less clogging. Also, embodiments of the present disclosure can achieve delivery molecules and/or particles with less specialized equipment than microinjection and nanoneedle injection, sometimes used for macromolecule delivery. Embodiments of the present disclosure can have less risk of cell death and aggregation than that of microfluidic devices based on diffusive delivery.

Embodiments of the present disclosure can include methods, systems, and devices for convective intracellular delivery of molecules. Methods for convective intracellular delivery can comprise one or more of the following steps: 1) providing a cell medium and a plurality of molecules to a microchannel, the cell medium comprising a plurality of cells; 2) flowing the cell medium through the microchannel at a flow velocity; 3) applying a convective intracellular delivery process as cell medium flows through the microchannel; 4) compressing the plurality of cells in a first compression gap, wherein the compressing causes the plurality of cells to undergo a loss in intracellular volume ($V_{loss}$); 5) applying at the first orthogonal surface a compressive force to the cells, wherein the compressive force causes the cells to undergo a first loss in volume ($V_{loss1}$); passing the plurality of cells to a first relaxation space, wherein the plurality of cells undergo a gain in volume ($V_{gain}$ or $V_{gain1}$); 6) applying a compressive force to the cells, wherein the compressive force causes the cells to undergo a second loss in volume ($V_{loss2}$); 7) collecting the plurality of cells at an outlet; and 8) collecting the plurality of cells at an outlet, wherein as the plurality of cells are collected they undergo a second gain in volume ($V_{gain2}$).

In some embodiments, the methods for convective intracellular delivery can comprise: providing a cell medium and a plurality of molecules to a microchannel, the cell medium comprising a plurality of cells; flowing the cell medium through the micro-channel at a flow rate, wherein as the cell medium flows through the micro-channel, the plurality of cells undergo a convective intracellular delivery process comprising: compressing the plurality of cells in a first compression gap, wherein the compressing causes the plurality of cells to undergo a loss in intracellular volume ($V_{loss}$); and passing the plurality of cells to a first relaxation space, wherein the plurality of cells undergo a gain in volume ($V_{gain}$) and absorb a portion of the plurality of molecules; and collecting the plurality of cells in an outlet.

In some embodiments, the methods for convective intracellular delivery of molecules can comprise providing a plurality of cells to a microchannel; flowing the plurality of cells to the microchannel; applying a compressive force to the cells, wherein the compressive force causes the cells to undergo a first loss in volume ($V_{loss1}$); passing the plurality of cells through a first relaxation space, wherein the plurality of cells undergo a first gain in volume ($V_{gain1}$); applying a compressive force to the cells, wherein the compressive force causes the cells to undergo a second loss in volume ($V_{loss2}$); and collecting the plurality of cells at an outlet, wherein as the plurality of cells are collected they undergo a second gain in volume ($V_{gain2}$).

Embodiments of the present disclosure may also include one or more systems for intracellular delivery of molecules. In some embodiments, the system may comprise a microchannel and a cell medium comprising a plurality of cells and a plurality of molecules, the cell medium flowing through the micro-channel at a flow rate, wherein as the cell medium flows through the micro-channel, the plurality of cells undergo a convective intracellular delivery process comprising: compressing the plurality of cells in a first compression gap, wherein the compressing causes the cells to undergo a loss in volume ($V_{loss}$); passing the plurality of cells to a first relaxation space, wherein the plurality of cells undergo a gain in volume ($V_{gain}$) and absorb a portion of the plurality of molecules.

Any of the above-described systems and methods may also include a cell comprising a plurality of macromolecules having an average diameter of 1 nm to 150 nm, the cell formed by any of the methods or systems described previously. In any of the above-described systems and methods, a plurality of macromolecules can be delivered to the plurality of cells. The plurality of macromolecules can be of uniform size or varying size. For instance, any molecule of the plurality of macromolecules can be from 1 nm to 100 nm, from 5 nm to 100 nm, from 10 nm to 100 nm, from 20 nm to 100 nm, from 30 nm to 100 nm, from 40 nm to 100 nm, from 50 nm to 100 nm, from 60 nm to 100 nm, from 75 nm to 100 nm, from 80 no to 100 nm, from 85 nm to 100 nm, from 90 nm to 100 nm, from 110 nm to 120 nm. In some embodiments the macromolecules can range in size from 3 kDa to 6 MDa, from 10 kDa, to 6 MDa, from 15 kDa to 6 MDa, from 20 kDa to 6 MDa, from 25 kDa to 6 MDa, from 30 kDa to 6 MDa, from 40 kDa to 6 MDa, from 50 kDa to 6 MDa, from 60 kDa to 6 MDa, from 70 kDa to 6 MDa, from 75 kDa to 6 MDa, from 80 kDa to 6 MDa, from 90 kDa to 6 MDa, from 100 kDa to 6 MDa, from 250 kDa to 6 MDa, from 500 kDa to 6 MDa, from 750 kDa to 6 MDa, 1 MDa to 5 MDa, 2 MDa to 4 MDa, 3 MDa.

Any of the above-described systems and methods can achieve convective intracellular delivery of molecules into a variety of cell types. These cell types may include, but are not limited to cells of the reproductive system, e.g. oocytes, spermatozoa, leydig cells, embryonic stem cells, amniocytes, blastocysts, morulas, and zygotes; leukocytes, e.g. peripheral blood leukocytes, spleen leukocytes, lymph node leukocytes, hybridoma cells, T cells (cytotoxic/suppressor, helper, memory, naive, and primed), B cells (memory and naive), monocytes, macrophages, granulocytes (basophils, eosinophils, and neutrophils), natural killer cells, natural suppressor cells, thymocytes, and dendritic cells; cells of the hematopoietic system, e.g. hematopoietic stem cells (CD34+), proerythroblasts, normoblasts, promyelocytes, reticulocytes, erythrocytes, pre-erythrocytes, myeloblasts, erythroblasts, megakaryocytes, B cell progenitors, T cell progenitors, thymocytes, macrophages, mast cells, and thrombocytes; stromal cells, e.g. adipocytes, fibroblasts, adventitial reticular cells, endothelial cells, undifferentiated mesenchymal cells, epithelial cells including squamous, limbal cells, cuboid, columnar, squamous keratinized, and squamous non-keratinized cells, and pericytes; cells of the skeleton and musculature, e.g. myocytes (heart, striated, and smooth), osteoblasts, osteoclasts, osteocytes, synoviocytes, chondroblasts, chondrocytes, endochondral fibroblasts, and perichonondrial fibroblasts; cells of the neural system, e.g. astrocytes (protoplasmic and fibrous), microglia, oligodendrocytes, and neurons; cells of the digestive tract, e.g. parietal, zymogenic, argentaffin cells of the duodenum, polypeptide-producing endocrine cells (APUD), islets of langerhans (alpha, beta, and delta), hepatocytes, and kupfer cells; cells of the skin, e.g. keratinocytes, langerhans, and melanocytes; cells of the pituitary and hypothalamus, e.g. somatotropic, mammotropic, gonadotropic, thyrotropic, corticotropin, and melanotropic cells; cells of the adrenals and other endocrine glands, e.g. thyroid cells (C cells and epithelial cells); adrenal cells; and tumor cells.

The cells may be Burkitt lymphoma cells, choriocarcinoma cells, adenocarcinoma cells, non-Hodgkin's B and T cell lymphoma cells, fibrosarcoma cells, neuroblastoma cells, plasmacytoma cells, rhabdomyosarcoma cells, carcinoma cells of the pharynx, renal adenocarcinoma, hepatoma cells, fibrosarcoma cells, myeloma cells, osteosarcoma cells, teratoma cells, teratomal keratinocytes, lung carcinoma cells, colon adenocarcinoma cells, lung adenoma cells, renal carcinoma cells, rectum adenocarcinoma cells, chronic myelogenous leukemia cells, ileocecal adenocarcinoma cells, hairy cell leukemia cells, acute myelogenous leukemia cells, colon carcinoma cells, cecum carcinoma and adenocarcinoma cells, leukemia-cecum adenocarcinoma cells, pancreatic carcinoma, Wilm's tumor cells, prostate adenocarcinoma cells, renal leimyooblastoma cells, bladder carcinoma cells, plasmacytoma cells, teratocarcinoma cells, breast carcinoma, epidermoid carcinoma of the cervix, ovarian teratocarcinoma, myeloma cells, T and B cell lymphoma cells, amalanotic melanoma cells, cervical carcinoma cells, rhabdomyosarcoma, hepatoma, medullary Thyroid carcinoma cells, malignant melanoma cells, glioblastoma cells, plasma cell leukemia, endometrial adenocarcinoma, squamous cell carcinoma, pancreatic adenocarcinoma, astrocytoma, gastric adenocarcinoma, pulmonary mucoepidermoid carcinoma cells, myeloid leukemia cells, EBV-transformed B cells, renal cell adenocarcinoma, acute leukemia, B cell plasmacytoma, acute lymphocytic leukemia, cutaneous T lymphoma, T cell leukemia, acute lymphoblastic leukemia, HIV+ T cells, medulloblastoma, B cells from sickle cell disease, acute monocytic leukemia, adrenocortical carcinoma, Bowes Melanoma and hepatocellular carcinoma.

The plurality of cells in any of the above-described systems and methods may include any of the above cells or derivatives thereof. While the presently described systems and methods are described in terms of biological cells, it is understood that these presently disclosed systems and methods can be achieved using a variety of materials other than biological cells, in some embodiments, the above-described systems and methods can be achieved with a variety of particles, including nanoparticles, intracellular probe sensors (e.g. molecular beacons and SmartFlares), viruses (e.g. lentivirus), and quantum dots.

Additionally, any of the above-described systems and methods can include any of the above-described cells suspended in a fluid, such as a cell medium. The cell medium can be any liquid in which a plurality of cells can be suspended and can include additional substances including one or more of a carbon source (e.g. glucose) water, various salts, a source of amino acids and nitrogen (e.g., beef, yeast extract). Additionally, the medium may include other nutrients such as plant count agar, nutrient agar, or trypticase soy agar.

Any of the above-described systems and methods can include flowing cells and/or cell medium through a microchannel. In some embodiments of the above-described systems and methods, the microchannel can be defined by a first wall and a second wall, the walls being substantially planar to each other. The microchannel may comprise a plurality of compressive surfaces protruding from the first wall. In some embodiments, the plurality of compressive surfaces can protrude outwardly from the first wall and towards a second wall. In some embodiments, the plurality of compressive surfaces can protrude outwardly from the second wall and towards a first wall. In some embodiments, the plurality of compressive surfaces can protrude outwardly from one of the first and second wall and towards one of the first and second wall. For instance, in some embodiments, the compressive surfaces can protrude normal from one or both of the walls. In other embodiments, the plurality of compressive surfaces can protrude from the first and/or second wall at an angle. In some embodiments, the plurality of compressive surfaces can protrude outwardly from both the first wall and the second wall. For example, each of the plurality of compressive surfaces can protrude outwardly from the first wall towards a second plurality of compressive surfaces protruding outwardly from the second wall. Additionally, in some embodiments of the above-described systems and methods, the plurality of compressive surfaces can define a plurality of compressive gaps. In some embodiments, the plurality of compressive surfaces may be a plurality of orthogonal surfaces. As such, in some embodiments, the microchannel of the above-described systems and methods can comprise a first orthogonal surface defining a first compression gap; and a second orthogonal surface defining a second compression gap.

Figure 1B:
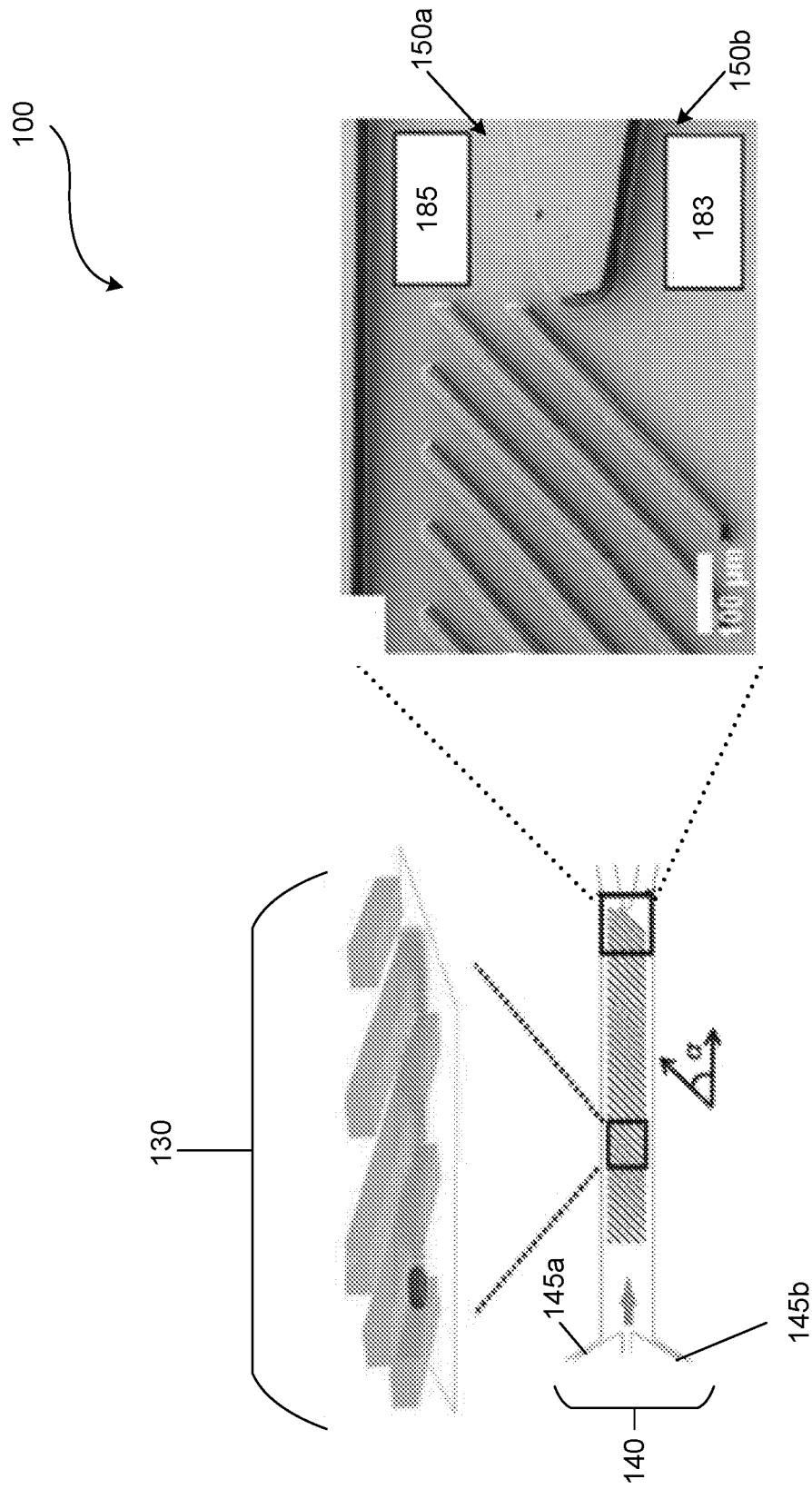
FIG. 1b is a schematic showing a two-outlet microchannel having a plurality of diagonal ridges, in accordance with one or more embodiments of the present disclosure.

An exemplary microchannel 100 for achieving convective intracellular delivery of any of the above-described systems and methods is illustrated in FIGS. 1a-1e. The above-described systems and methods may include some or all of the features described below with respect to FIGS. 1a-1e. As shown in FIG. 1a, the microchannel 100 can comprise a first planar wall 110 and a second planar wall 120. The first planar wall 110 can comprise a plurality of compressive surfaces 130 protruding outwardly from the first planar wall 110. The microchannel 100 can comprise one or more inlets 140 provided for flowing a plurality of cells 180 and a plurality of particles 190 into the microchannel 100. In some embodiments, and as illustrated at FIG. 1b, the one or more inlets 140 may include a sheath flow inlet 145a, 145b for delivering a sheath flow fluid into the microchannel 100. The microchannel 100 can comprise a plurality of outlets 150 for collecting portions of the plurality of cells 180.

Figure 1C:
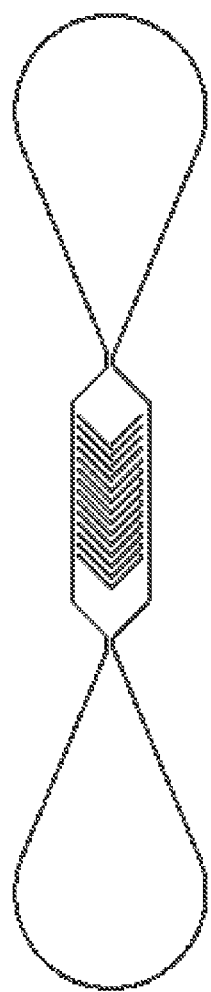
FIGS. 1c and 1d show various microchannels having chevron-patterned ridges, in accordance with one or more embodiments of the present disclosure.

The microchannel can comprise a plurality of compressive surfaces 130. In some embodiments, the plurality of compressive surfaces 130 can comprise a plurality of ridges, as illustrated at FIG. 1b. In some embodiments, the plurality of compressive surfaces 130 may be diagonally-oriented with respect to a central flow axis, as illustrated in FIG. 1b. The central flow axis can be located proximate a central portion of the microchannel 100 and comprise an axis running parallel to a primary flow through the microchannel 100. As illustrated at FIG. 1b, in some embodiments, the plurality of compressive surfaces 130 can extend parallel to each subsequent ridge of the plurality of ridges. The plurality of compressive surfaces 130 may be straight, but need not be. For instance, the plurality of compressive surfaces 130 can be any shape, including but not limited to rectangular, cylindrical, trapezoidal, or triangular. In some embodiments, the plurality of compressive surfaces may be orthogonal. For instance, in some embodiments, the plurality of compressive surfaces may have at least one right angle. In some embodiments, as illustrated at FIGS. 1c and 2d, the plurality of compressive surfaces 130 may form a chevron pattern. Additionally, as will be understood by those skilled in the art, the plurality of compressive surfaces can comprise at least one ridge, but need not all be ridges.

The plurality of compressive surfaces 130 may define a compression gap 170 between a compressive surface 130 and a surface of an opposing wall 120. For instance, in an embodiment wherein the plurality of compressive surfaces 130 protrudes from the first planar wall 110, the plurality of compressive surfaces 130 may define a compression gap 170 between a compressive surface 130 and a surface across from the compressive surface 130 on the second planar wall 120. As used herein, a surface may include the closest or nearest portion of the opposing wall, for example where the wall does not otherwise have corresponding ridges or protrusions. In some embodiments, the second planar wall 120 can comprise a plurality of compressive surfaces 130, and the opposing surface can be, for example, an opposing compressive surface 130. The compression gap 170 can therefore be defined as the space formed between a compressive surface 130 and a surface of the second wall 120, or the space between opposing compressive surfaces on opposing walls. In some embodiments, the opposing ridges can be aligned with each other.

While the first and second walls of the microchannel are described with respect to FIGS. 1a-1e as being planar, they need not be. For instance, in any of the above-described systems and methods, the first and second walls can be substantially planar. In other words, they can be slightly angled towards or away from each other such that they converge or diverge across a length of the microchannel. In some embodiments, they can converge or diverge more than slightly. Additionally, while the first wall can be oriented on a top portion of the microchannel and the second wall can be oriented on a bottom portion of the microchannel, they need not be so arranged and it is contemplated that the first wall can be oriented on a bottom portion of the microchannel and the second wall may be oriented on a top portion of the microchannel.

The size of the compression gap 170 can be increased or decreased as desired, based on device design. In some embodiments, the size of the compression gap 170 can be defined in terms of the average diameter of a cell. As will be understood, the diameter of the cell can be defined as the largest distance between two points on a cell. In some embodiments, the height of the compression gap may be defined based on a percentage of the average cell diameter. For instance, the compression gap 170 may have a height of about 10% about 80% an average cell diameter, about 10% about 50% an average cell diameter, about 10% to about 40% an average cell diameter, about 10% to about 30% an average cell diameter, about 10% to about 20% an average cell diameter, about 20% to about 30% an average cell diameter, about 30% to about 40% an average cell diameter, about 40% to about 50% an average cell diameter, about 50% to about 60% an average cell diameter. In some embodiments, the height of the compression gap 170 can be about 15%, about 20% about 25%, about 30%, about 35%, about 40%, about 45%, about 50%, about 55%, or about 60%, about 65%, about 70%, about 75%, or about 80% an average cell diameter. The average cell size can refer to average of the largest cross-sectional dimension of the cells flowed through the sorting device, and can be calculated using. In some embodiments, the average cell diameter can be measured using a variety of tools now known or later discovered including but not limited to optical microscopy, confocal microscopy, coulter counter, and flow cytometry.

As shown in FIGS. 1a and 1b, the plurality of compressive surfaces 130 may be separated by a relaxation space 160. The relaxation space 160 can comprise the width of a space or channel formed between a first compressive surface of the plurality of compressive surfaces and a second compressive surface of the plurality of compressive surfaces. In some embodiments, the relaxation space 160 may be from 50 to about 1000 microns, from 50 to 750 microns, from 50 to 500 microns, from 50 to 400 microns, from 50 to 350 microns, from 100 to 300 microns, from 100 to 750 microns, from 100 to 500 microns, from 100 to 400 microns, from 100 to 300 microns, 100 to 250 microns, or from 125 to 250 microns. The relaxation space 160 can be at least 50 microns, at least about 100 microns, at least 125 microns, at least 150 microns, at least 250 microns, or at least 300 microns. The relaxation space 160 can be up to 20 microns, up to 100 microns, up to 200 microns, up to 300 microns, up to 1000 microns up to 750 microns, or up to 500 microns, 50 to 350 microns, from 100 to 300 microns, from 100 to 250 microns, from 125 to 250 microns, or at least 300 microns.

The plurality of compressive surfaces 130 may comprise an angle ($\alpha$), as illustrated at FIG. 1b. The plurality of compressive surfaces 130 can be inclined at an angle to create hydrodynamic circulations underneath the compressive surfaces 130 and can be designed to compress and translate cells normal to the flow direction. The angle of the compressive surfaces 130 can also affect the trajectories of cells. The angle may vary depending on one or more parameters including, but not limited to, the types of cells flowed through the microchannel, the relaxation space 160, and the flow velocity of the medium flowed through the microchannel 100. As such, adjusting the angle may facilitate migration of cells along the compressive surfaces 130. For instance, adjusting the angle may facilitate movement of dead or damaged cells to the sides of the microchannel 100 in order to prevent clogging of the microchannel 100.

The angle may be increased or decreased, based on device design. For instance, in some embodiments, the angle can be from 20 to 90 degrees, from 20 to 75 degrees, from 30 to 60 degrees, from 30 to 45 degrees, from 45 to 60 degrees, at least 30 degrees, at least 45 degrees, at least 60 degrees, at least 75 degrees. The angle of each respective compressive surface may also be the same or different along a length of the microfluidic device. In instances where a compressive surface 130 is not linear, the angle can be measured based on a line that is a linear fit to the non-linear ridge.

The number of compressive surfaces 130 in the microchannel 110 can be increased or decreased as desired. In some embodiments, the microchannel 110 can comprise 1 to 100 compressive surfaces 130. In some embodiments, the microchannel 110 can comprise at least 3 compressive surfaces 130, at least 4 compressive surfaces 130, at least 5 compressive surfaces 130, at least 6 compressive surfaces 130, at least 7 compressive surfaces 130, at least 8 compressive surfaces 130, at least 9 compressive surfaces 130, or at least 10 compressive surfaces 130. In some embodiments, the microchannel 110 can comprise up to 100 compressive surfaces 130, up to 75 compressive surfaces 130, up to 50 compressive surfaces 130, or up to 40 compressive surfaces 130. In some embodiments, the microchannel 110 can include 5 to 50 compressive surfaces 130, 7 to 40 compressive surfaces 130, or 7 to 21 compressive surfaces 130. In some embodiments, the microchannel 110 can comprise about 14 compressive surfaces 130.

The plurality of compressive surfaces 130 can be described by a thickness. The thickness can be defined as the linear measurement of the compressive surface in the direction of primary flow. The thickness can be increased or decreased as desired. In some embodiments, the thickness can be from about 7 to about 30 microns, from about 7 to about 20 microns, from about 7 to about 18 microns, from about 7 to about 16 microns, from about 7 to about 11 microns, from about 7 to about 9 microns, from about 20 to about 30 microns, from about 22, to about 28 microns, from about 24 to about 28 microns, from about 18 to about 21 microns, from about 16 to about 22 microns, or from about 8 to about 11 microns. In some embodiments, the thickness can be at least about 9 microns, at least about 11 microns, and at least about 16 microns.

The microchannel 100 can have one or more inlets 140. The one or more inlets 140 may be located on a first side wall of microchannel 100. In some embodiments, the microchannel 100 can have a cell inlet 140 and a sheath flow inlet 145a, 145b. In some embodiments, the cell inlet can be located between a first sheath flow inlet 145a and a second sheath flow inlet 145b, or can be surrounded by a first sheath flow inlet 145aa. In some embodiments, the cell inlet 140 can be downstream from one or more sheath flow inlets 145a, 145b, or can be aligned with one or more sheath flow inlets 145a, 145b. A sheath fluid can allow for hydrodynamic focusing of the cell medium. The one or more sheath flow inlets 145a, 145b can be located proximate the cell flow inlet 147, or upstream of the cell flow inlet 147. Focusing the cells in the inlet can comprise providing a sheath fluid to the sheath flow inlets 145a, 145b until the sheath fluid reaches laminar flow and then subsequently introducing the cell medium cell medium through the cell inlet 147. The cells can be introduced into the cell inlet 147 by injection, for example by syringe pumps.

Figure 1D:
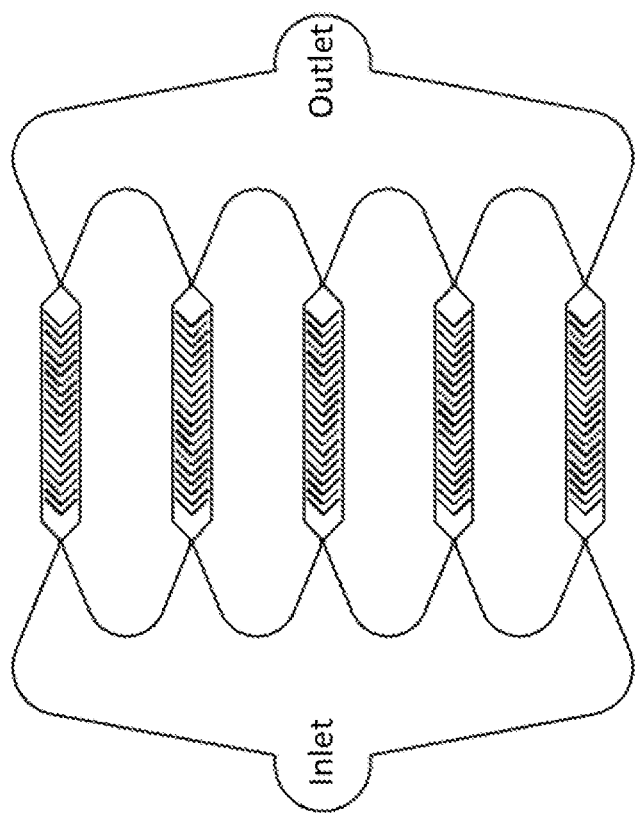

The described microchannel 100 can be constructed in a variety of ways. In one exemplary non-limiting embodiment, the microchannel can be made using a replica molding of polydimethylsiloxane (PDMS) on a permanent mold. The mold can be created by two-step photolithography patterning of a photoresist on a 4-inch-diameter silicon wafer. After the removal of PDMS from the mold, inlet and outlet holes can be punched in the side walls of the PDMS, and the PDMS can be subsequently bonded to a glass substrate to form the microfluidic channel. Additionally, in some embodiments as illustrated at FIG. 1d, the systems and methods can include more than one microchannel to allow for increased and simultaneous performance of the above-described methods.

The plurality of cells 180 can be flowed into the microchannel 100 at a flow velocity. The flow velocity of any of the systems and methods described previously can be increased or decreased as desired. As used herein, the flow velocity can describe the velocity of the cell medium at an inlet or at an outlet. The flow velocity can be from about 3 to about 1000 mm/s, from about 3 to about 500 mm/s, from about 3 to about 250 mm/s, from about 3 to about 100 mm/s, from about 3 to about 50 mm/s, from about 3 to about 25 mm/s. The flow velocity can be at least about 3 mm/s, at least about 20 mm/s, at least about 50 mm/s, at least about 100 mm/s, or at least about 500 mm/s. The flow velocity can be about 3 mm/s, about 20 mm/s, about 500 mm/s, or about 1000 mm/s. The flow velocity can also be adjusted as a function of the length of the channel, and/or the size of the relaxation space, based on design preferences. For instance, increasing the length of the channel can allow for a greater flow velocity. Increasing the velocity in similarly sized devices can result in increased pressure within the device. By increasing the length of the microchannel, the increased pressure can be accounted for while permitting higher flow velocity. For instance, increasing the relaxation space can permit increasing the flow velocity as the greater space allows the cells a longer distance over which to travel and be subjected to secondary flow in the ridge channels. As such, increased relaxation space can permit an increased relaxation time and positive lateral displacement for certain cells despite greater flow velocity. In some embodiments, the plurality of cells 180 can be flowed into the microchannel 100 at a flow rate. The flow rate can be 3 to 1500 mm/s.

Figure 1E:
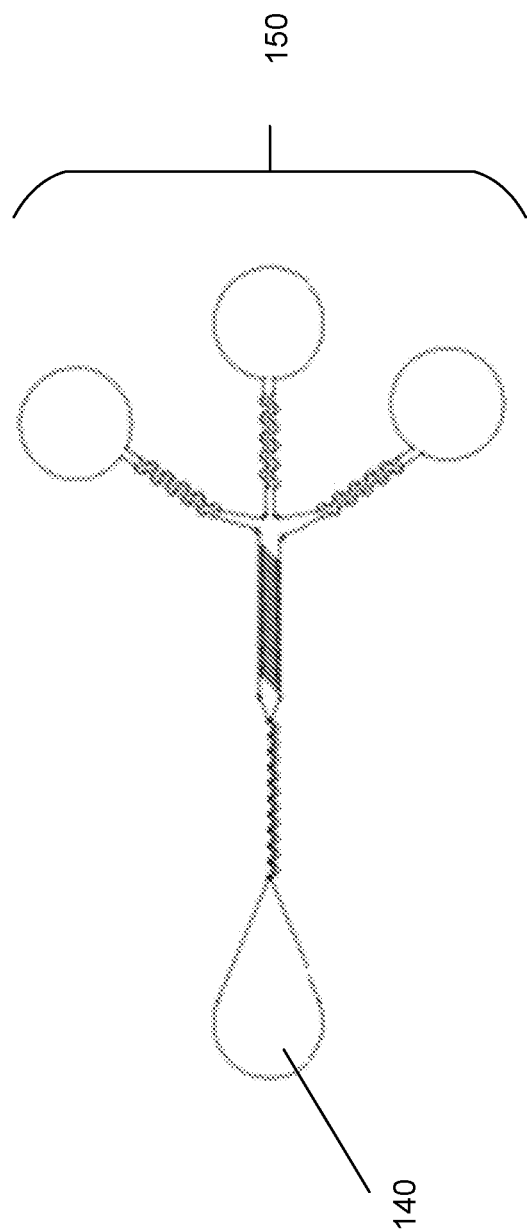
FIG. 1e shows a three-outlet microchannel, in accordance with one or more embodiments of the present disclosure.

The microchannel can comprise a plurality of outlets 150a, 150b for collecting portions of the plurality of cells. As illustrated at FIG. 1b, one outlet may collect processed cells 183 that have successfully had a plurality of particles intracellularly deliver, described in greater detail below. Additionally, as illustrated at FIG. 1b, another outlet may collect dead or damaged cells 185. By having a dual-outlet system and modes of secondary flow (e.g. relaxation spaces between subsequent compressive spaces), the presently described systems and methods can achieve high-throughput molecular delivery without the risk of clogging of the system. In other embodiments, the microchannel 100 may comprise two or more outlets. For instance, FIG. 1e illustrates an embodiment with one inlet and three outlets 150. In some embodiments, the microchannel 100 can comprise at least two outlets, at least three outlets, at least four outlets or at least five outlets. The number of outlets can be two, three, four or five. As such, in addition to molecular delivery, it is contemplated that the system may also achieve sorting functionalities, such as sorting by biomechanical properties, such as viscoelasticity, stiffness, or elasticity, or adhesion by coating the microchannel in a cell adhesion entity.

Any of the above-described outlets can include a well or chamber for pooling and/or pipetting them in the direction of a chamber or directly to a chamber. In other embodiments, the outlets can be further integrated with additional processing steps, as described below, through an integrated chip or through a capillary. Additionally, after cells are collected, any of the above-mentioned systems and methods can include an additional step of analyzing the cells using any analysis tool now known or later discovered including but not limited, flow cytometry, fluorescence microscopy, functional assays (e.g., apoptosis, cell cycle, viability, proliferation, angiogenesis, spectroscopy, immunoassays, and microplating. Additionally, in some embodiments, the microchannel and cells can be analyzed with electrode counters and microscopy.

As discussed previously, any of the above-described systems and methods can comprise flowing a plurality of cells through the microchannel 100 at a flow velocity. As the cells flow through the microchannel 100, the cells can undergo a convective intracellular delivery process. This process can be characterized by one or more compressions of the plurality of cells followed by a relaxation period. For instance, as described previously, the convective intracellular delivery process can comprise compressing the plurality of cells in a first compression gap, wherein the compressing causes the plurality of cells to undergo a loss in intracellular volume ($V_{loss}$) and passing the plurality of cells to a first relaxation space, wherein the plurality of cells undergo a gain in volume ($V_{gain}$) and absorb a portion of the plurality of molecules. As will be understood by those skilled in the art, depending on the number of compressive surfaces and relaxation spaces, the convective intracellular delivery process can occur one or more times.

Any of the above-described systems and methods can include bulk volume flow across the cell membrane, such that when the cells are compressed by a compressive surface the cells abruptly undergo a compressive force such that cell cytoplasm is transported in bulk volume flow out of the cell. This transfer out of the cell may be characterized as $V_{loss}$. In some embodiments, $V_{loss}$ can be characterized in terms of an initial cell volume before compression. Initial cell volume before compression can be measured using a variety of tools now known or later discovered including but not limited to optical microscopy, confocal microscopy, coulter counter, and flow cytometry. In an embodiment, $V_{loss}$ may be 30%, 25%, 20%, 15%, or 10% the initial volume of the cell. In some embodiments, $V_{loss}$ can be at least 10%, at least 15%, at least 20%, at least 25%, or at least 30% the initial volume of the cell. The transfer of volume back into the cell may be characterized as $V_{gain}$. In any of the above-described systems and methods, $V_{gain}$ can be described in terms of $V_{loss}$ such that $V_{gain}$ can be at least 10%, at least 15%, at least 20%, at least 25%, at least 30%, at least 40%, at least 50%, at least 60%, at least 70%, at least 75%, at least 80%, at least 90%, or at least 100% $V_{loss}$. In any of the above-described systems and methods, $V_{loss}$ can occur in at least 1 microsecond, at least 2 microseconds, at least 3 microseconds, at least 4 microseconds, at least 5 microseconds, at least 6 microseconds, at least 7 microseconds, at least 8 microseconds, at least 9 microseconds, at least 10 microseconds, at least 15 microseconds, at least 20 microseconds, at least 25 microseconds, at least 30 microseconds, at least 45 microseconds, at least 50 microseconds. Additionally, any of the above-described systems and methods can cause a cell to undergo multiple losses in volume and multiple gains in volume based on the number of compressive surfaces. In some embodiments, a cell may regain 100% $V_{loss}$ in from 1 to 100 ms, from 4 to 100 ms, from 10 to 100 ms, from 15 to 100 ms, from 20 to 100 ms, from 25 to 100 ms, from 30 to 100 ms, from 40 to 100 ms, from 50 to 100 ms, from 60 to 100 ms, from 75 to 100 ms, from 80 to 100 ms, and from 90 to 100 ms, Additionally, it is contemplated that the time taken to regain 100% $V_{loss}$ may vary with the cell type, therefore the time may be more or less depending on the type of cell. Therefore, the plurality of cells may undergo $V_{loss1}$, $V_{loss2}$, $V_{loss3}$, $V_{loss7}$, $V_{loss14}$, $V_{loss21}$, up to $V_{lossN}$. As such the plurality of cells may undergo $V_{gain1}$, $V_{gain2}$, $V_{gain3}$, $V_{gain7}$, $V_{gain14}$, $V_{gain1}$, up to $V_{gainN}$ depending on the number of relaxation spaces which corresponds to the number of compressive surfaces.

Additionally, the convective intracellular delivery process of any of the above-described methods can include intracellular delivery of extracellular molecules. Molecules may comprise a variety of entities including but not limited to particles, macromolecules, nanoparticles, dextran, plasmids, mRNA, or beads.

While the above-mentioned embodiments are described with respect to compressing cells within a microchannel, it is understood that any of the above-described systems and methods can obtain transient volume change through other approaches including inertial contact of a cell with a wall (including slamming, thrusting, or otherwise forcing contact between a cell and a wall), rapid compressions with non-solid force fields including fluid or acoustic fields.

EXAMPLES

The present disclosure is also described and demonstrated by way of the following examples. However, the use of these and other examples anywhere in the specification is illustrative only and in no way limits the scope and meaning of the disclosure or of any exemplified term. Likewise, the disclosure is not limited to any particular preferred embodiments described here. Indeed, many modifications and variations of the disclosure may be apparent to those skilled in the art upon reading this specification, and such variations can be made without departing from the disclosure in spirit or in scope. The disclosure is therefore to be limited only by the terms of the appended claims along with the full scope of equivalents to which those claims are entitled.

Example 1

Methods

Device Design

The microfluidic device design used constrictions in the form of angled ridges in a single large channel for the rapid processing of high numbers of cells. The large channel allowed a multitude of cells to pass simultaneously under each ridge while hydrodynamic drag forces maintained cell velocity through the constrictions, allowing cell processing to continue rapidly even after many constrictions. The angled ridges also served as an escape mechanism for nonviable cells and cell aggregates that would otherwise clog the device or dilute the processed cell population. Therefore, this design functioned effectively even with localized clogs, and rapidly self-cleared. A multi-channel design of this device successfully processed 50 million cells in 10 minutes without clogging.

Fabrication of Microfluidic Channels

The microfluidic features of this device were molded onto polydimethylsiloxane (PDMS) and plasma bonded to a glass slide. A reusable SU-8 mold was made using standard two-step photolithography on a silicon wafer. Constriction gaps of 50-60% of the average relaxed cell diameter (14.5±1.5 μm) were used for optimal delivery, but gaps of 40-130% of the average cell diameter were also studied. The cell inlet flow directed cells through the constrictions, preventing the cells from preferentially flowing around the ridges without compressing. To fabricate the devices, a 10:1 ratio of PDMS and crosslinking agent was mixed and poured onto the SU-8 mold to form the microfluidic channel features by replica molding. The PDMS was then degassed in a vacuum chamber and cured for 6 hrs at 60° C. The cooled PDMS was then removed from the molds and outlets and inlets were punched using biopsy punches. The PDMS was then bonded to sonicated glass slides using a plasma bonder (PDC-32G Harrick) followed by 1 hr in a 60° C. oven. After cooling, the channels were passivated using 1% bovine serum albumin (BSA) for an overnight incubation at 4° C.

Cell Culture

K562 cells (CCL-243) from ATCC were cultured in RPMI-1640 supplemented with 10% fetal bovine serum (FBS) and 1% penicillin-streptomycin. PC3 prostate cancer cells (CRL-1435) were cultured in F-12K with 10% FBS and 1% penicillin-streptomycin. The cells were incubated at 37° C. with 5% CO2. The PC3 cells were passaged using 0.25% Trypsin-EDTA. Primary leukocytes were isolated from whole donor blood by density gradient centrifugation. Whole donor blood was centrifuged at 700 RCF for 10 mins with Ficoll density centrifugation media and the concentrated leukocyte band (buffy coat) was collected.

Microfluidic Experimental Setup

A cell flow buffer consisting of DPBS (−/−) with 0.1% BSA, 0.04% EDTA, and trace Tween 20 was used to maintain a single-cell suspension throughout the experiment. Experiments performed using pure DPBS (−/−) and serum-free RPMI-1640 without BSA, EDTA, or Tween determined that these agents had no observable effect on molecular delivery. Transfection and RNA probe delivery experiments were done using Opti-MEM and serum-free RPMI-1640, respectively. The cells were isolated from culture media and resuspended in buffer at ~5×10⁶ cells/mL with the desired concentration of target molecules. The cell-buffer suspension was infused into the microfluidic device at a controlled rate using syringe pumps. Following collection from the outlets, the cells were washed 2× with DPBS (−/−) to remove residual molecules external to the cells.

High-Speed Video Microscopy

The experiments were carried out on the stage of an inverted bright-field microscope (Eclipse Ti, Nikon), with a high-speed camera attachment (Phantom v7.3, Vision Research). High speed (~5,000 fps) videos were taken of cells during processing at various segments of the device.

Video Analysis for Cell Volume Change

To measure the cell volume inside the device, measurements were taken of the cell area from video data and applied volume assumptions based on a cell deformation model. A custom cell tracking algorithm was used to automatically track the trajectory and area of cells in the video, with manual measurements used to verify. For each tracked cell, the algorithm identified all video frames where the cell was visible, and extracted the position and number of pixels it occupied (area). For each manual measurement, the ellipse that fit to the pixels of the sharpest gray scale intensity gradient to represent the maximum projected cell boundary was taken. The length scales of each image were calibrated based on known ridge dimensions, which enabled translation of the number of pixels into an area measure. For each cell, the area before it entered the ridge region of the device was measured to determine its uncompressed volume and the area when completely under each ridge to determine the compressed volumes. The volume of the unperturbed cell was taken as an ellipsoid where the projected area of the ellipse was revolved about the major axis, resulting in the minimum reasonable volume for the unperturbed cell. To take the compressed cell measurements, the same revolved ellipsoid procedure was applied to the compressed cell area and cut equal caps that represent the volume of the ellipsoid that intersected with the constraints of the ridge and channel bottom. This was considered the maximum reasonable volume for the compressed cell as it approached the cylindrical case for smaller gap sizes and collapsed back to the unperturbed ellipsoid case for larger gap sizes.

Flow Cytometry

The BD Accuri C6 Flow Cytometer was used to characterize cell uptake of fluorescent target molecules. Samples processed with FITC-dextran or GFP RNA or plasmid were excited with a 488 nm wavelength laser and emission was detected with a 533/30 filter. Samples with cyanine-3 were excited with a 488 nm laser and detected by a 585/40 filter. The viability of the cells was tested by staining with 2 μM EthD-1 solution34, 35. EthD-1 stained cells were excited at 640 nm and detected with a 670 LP filter.

Confocal Microscopy

Confocal microscopy of cells with tetramethylrhodamine (TRITC)-dextran was performed using the Zeiss LSM 700 to determine the intracellular localization of the delivered dextran molecules. The Zeiss 710 NLO with a 40× water lens was used to image K562 cells with Cy3-plasmid and 100 nm nanoparticles. These cells were stained with DiO membrane stain and Hoechst nucleus stain per manufacturer protocol.

Atomic Force Microscopy

Measurements of the viscous relaxation of individual cells during repeated compressions were performed using an MFP-3D AFM in concert with an inverted optical microscope (Nikon Ti) to optically align the AFM probe with the center of each cell. The probes used in this study were MLCT-O10-D probes with a nominal spring constant of 0.03 N/m. The AFM cantilever interacted with the cells via a 15 μm diameter PMMA microsphere. Cantilever calibration was performed using the thermal vibration method against a glass surface. K562 cells in culture media were adhered to the surface of a glass Fluorodish using Cell-Tak. The indentation depth was chosen to be 10 µm to simulate the strain imposed by a 5 µm gap in a microfluidic channel. The cell relaxation constant was extracted from the decay of viscous forces acting on the probe while maintaining constant indentation for 2 seconds after compression.

Results

Microfluidic Cell Deformation

Cell deformation was caused by microfluidic flow through ridges with rectangular cross-section that were repeated within a microchannel to precisely exert abrupt and brief compressions upon cells. Hydrodynamic forces maintained high cell velocity throughout multiple constrictions, while the angled ridges removed dead cells and clusters of cells which could cause occlusions.

Figure 2:
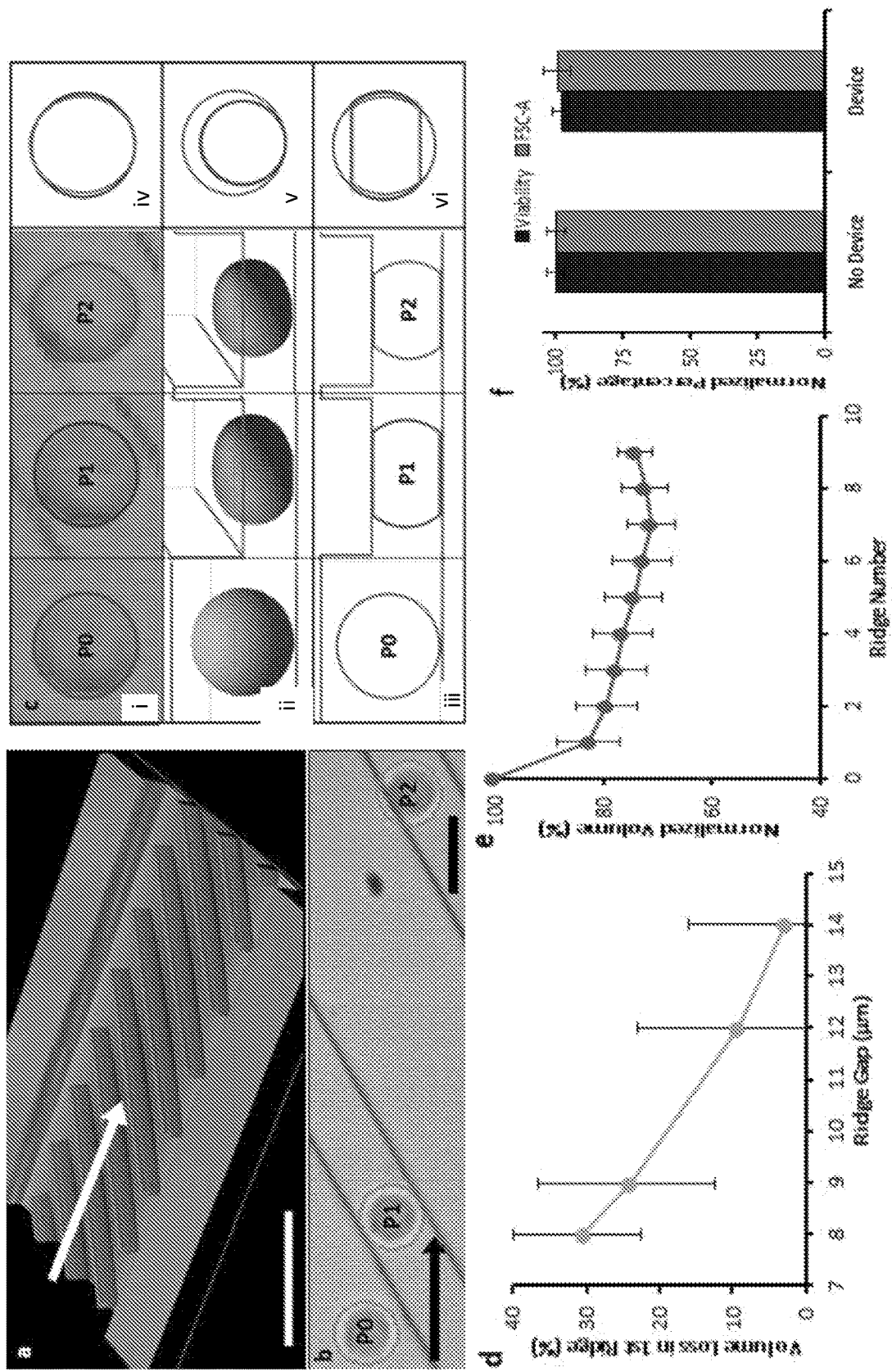
FIG. 2 shows various images and graphical representations characterizing device and cell volume measurement, in accordance with one or more embodiments of the present disclosure.

FIG. 2 at (a) shows profilometric images of the microfluidic channel layout with diagonal ridges. The arrow indicates cell flow direction. As cells encountered the rectangular ridges, abrupt shape change was observed as cells compress under the ridges to conform to a gap that is smaller than their diameter (FIG. 2 at (a)). Cell compression time was determined by convolution of the cell with a sharp edge of the ridge (<1 µm as determined by optical profilometry) at the measured cell velocity (~100 mm/s). During this time, cells were observed to compress vertically up to 70%, for a vertical compression velocity on the order of 1 m/s. The abrupt shape change caused by the sharp deformation structure of the rectangular ridge was quantitatively analyzed by high speed video analysis (FIG. 2 at (b)). FIG. 2 at (b) shows an overlay of a single cell (outlined in red) at multiple positions passing through the ridges.

Measurement of Cell Volume Change

Using a computational cell deformation model combined with area analysis of high speed videos of individual cells in the microfluidic channel, the change in cell volume was evaluated at several points in the channel (FIG. 2 at (c)). FIG. 2 at (c) shows image analysis of a single cell inside the device. Measurements were taken of K562 myeloma cell area before compression, and then when entirely constrained under each ridge (FIG. 2 at (ci)). Before compression, each cell was approximated as an ellipsoid, while the cell shape under each ridge was approximated to a truncated ellipsoid, as determined by a cell deformation model (FIG. 2 at (cii), (ciii)). The compressed cell height was equal to the ridge gap, which was independently measured by profilometry. Due to the uncertainty of cell shape and orientation between ridges, the cell volume between ridges cannot be deduced from its area measurement.

From the known gap and modeled cell shape, the cell volume before and during compressions was determined. An overlay of cell area measurements at the various positions shows subtle area change, suggesting that the vertical constraint from the ridge mainly accounts for the volume change (FIG. 2 at (civ)). A view of spherical cells with the same volume as the compressed cells visualizes the volume change when projected on the pre-compression cell (FIG. 2 at (cv)). Cells exhibited the most significant volume decrease at the first ridge due to the sudden change in shape from ellipsoid to truncated ellipsoid (FIG. 2 at (cvi)). Decreasing the gap size of the microfluidic device led to a greater volume decrease between the pre-compression cell and the cell compressed under the first ridge (FIG. 2 at (d)). FIG. 2 at (d) shows that the percent of cell volume that was lost under the first ridge increased with smaller device ridge gap, n>250, bars are interquartile range. The cell volume proceeded to slightly decrease with each subsequent compression to a plateau volume after approximately 8 ridges (FIG. 2 at (e)). FIG. 2 at (e) shows normalized volume of cells at different ridge positions in the channel, n>45, bars are standard deviation.

Figure 3:
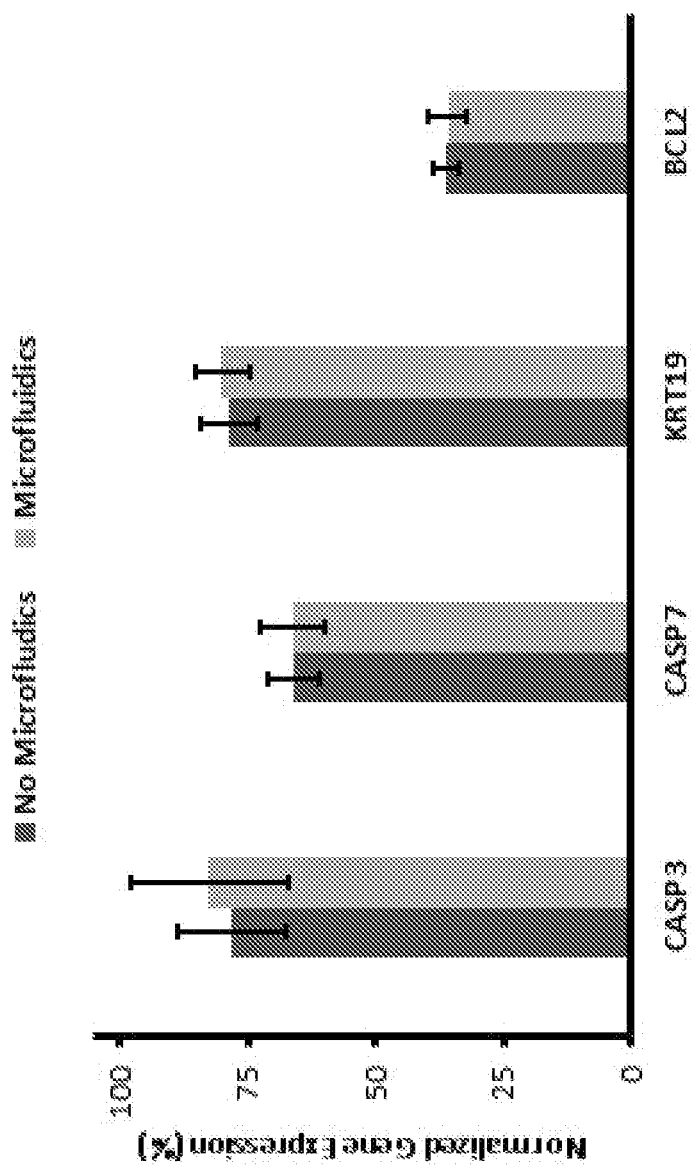
FIG. 3 shows a comparison of gene expression showing the cell viability and integrity is unaffected by the presently disclosed systems and methods, in accordance with one or more embodiments of the present disclosure.

While the volume was observed to decrease by up to 30% during compressions, cells were quickly restored to their initial size with little impact on cell integrity, viability, and related gene expression. After microfluidic processing, cell culturing and expansion was successfully conducted with no change in cell growth rate. Flow cytometry analysis <30 min after processing showed that the compression experiments have negligible impact on forward scatter measurements of cells (FIG. 2 at (f)). FIG. 2 at (f) shows flow cytometry forward scatter measurements showed minimal impact by device, viability stain showed device processing caused <5% cell death, n=2. Ethidium homodimer-1 (EthD-1) staining of processed cells showed <5% cell death compared to the No Device group (FIG. 2f). RT PCR was used to further quantify that the compressions in the microchannel did not impact the expression of apoptotic, cytoskeletal, and other signaling genes (FIG. 3). A separate, detailed study on cell viability after rapid compressions, including expression of apoptotic genes, was consistent with this observation. FIG. 3 shows that Expression of genes related to cell viability and integrity is unaffected by the presently described systems and methods. RT PCR showed that RNA expression of apoptosis-related and cytoskeletal genes is unaffected by the microfluidic processing. Expression data was normalized with respect to KRT10. These results suggested that cells recovered normal volume and function after the brief volume loss.

Characterizing Volume Exchange Through Molecular Delivery

The volume reduction of compressed cells indicated that a portion of cytosol was expelled from the cell interior. Cell volume recovery, on the other hand, requires extracellular fluid to enter the cell. Since the video analysis does not allow for evaluation of cell volume in between the ridges, the dynamics of volume exchange was further characterized by transmembrane fluid transfer using fluorescently labeled dextran (Sigma-Aldrich) as a tracker molecule. Dextran of various sizes was added to the cell suspension immediately before compression experiments. It was hypothesized that the cell relaxations after each compression will cause the extracellular fluid to enter the cell interior transporting dispersed fluorescent molecules, and that the molecules will partially remain in the cell interior after consecutive compressions serving as an indicator of volume exchange.

Figure 4A:
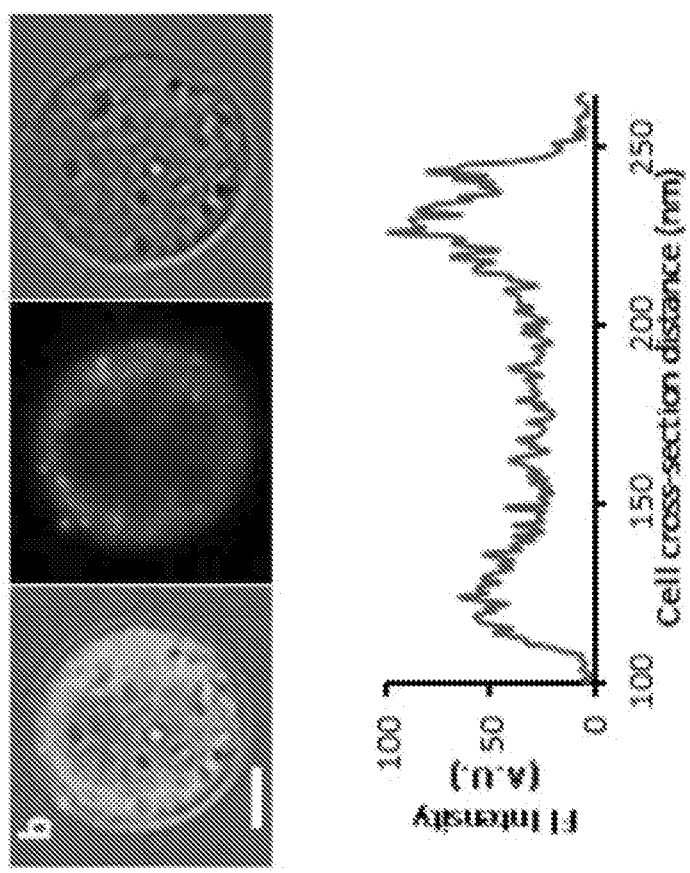
FIGS. 4a and 4b show various images and graphical representations characterizing molecular delivery based on ridge gap, percent volume change, flow rate, and time between ridges, in accordance with one or more embodiments of the present disclosure.
Figure 4B:
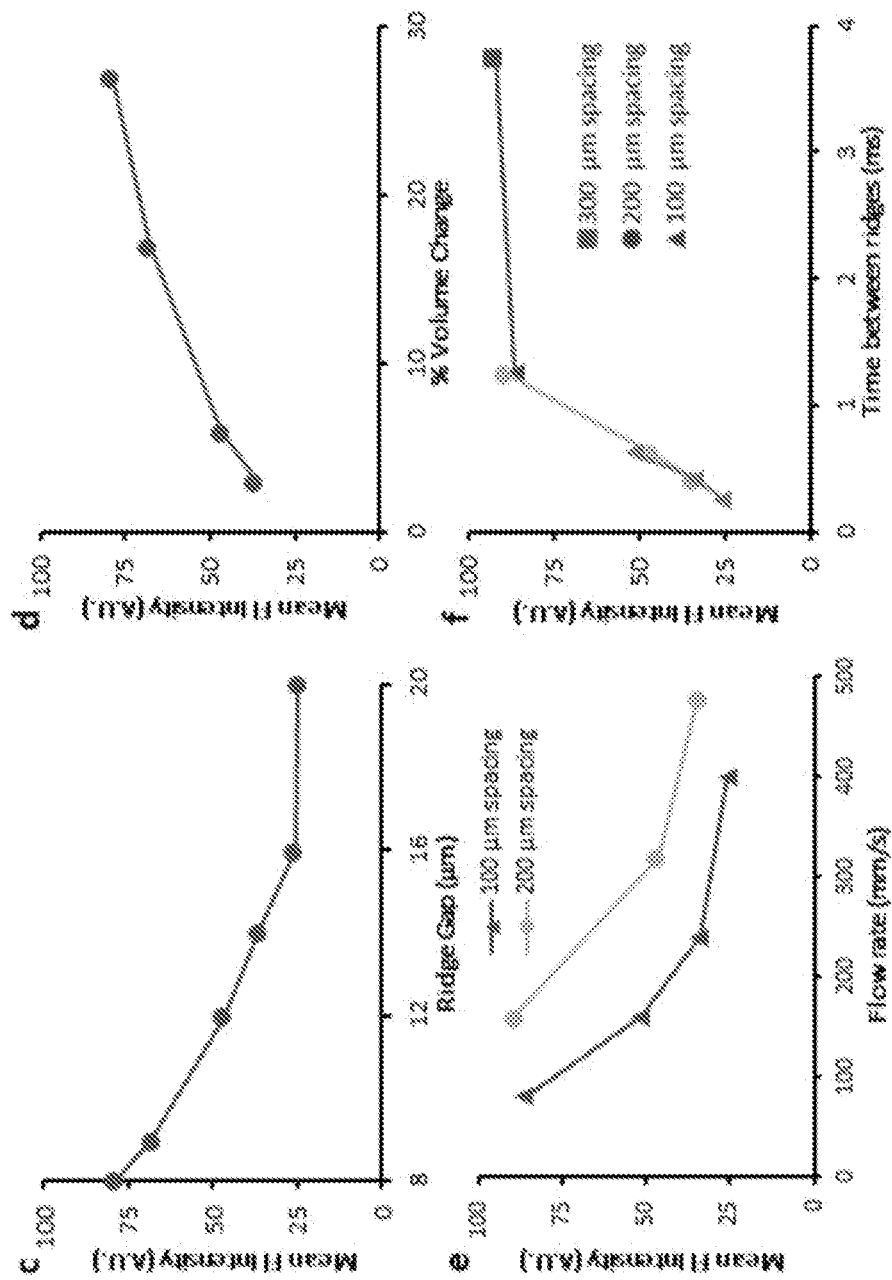
Figure 5A:
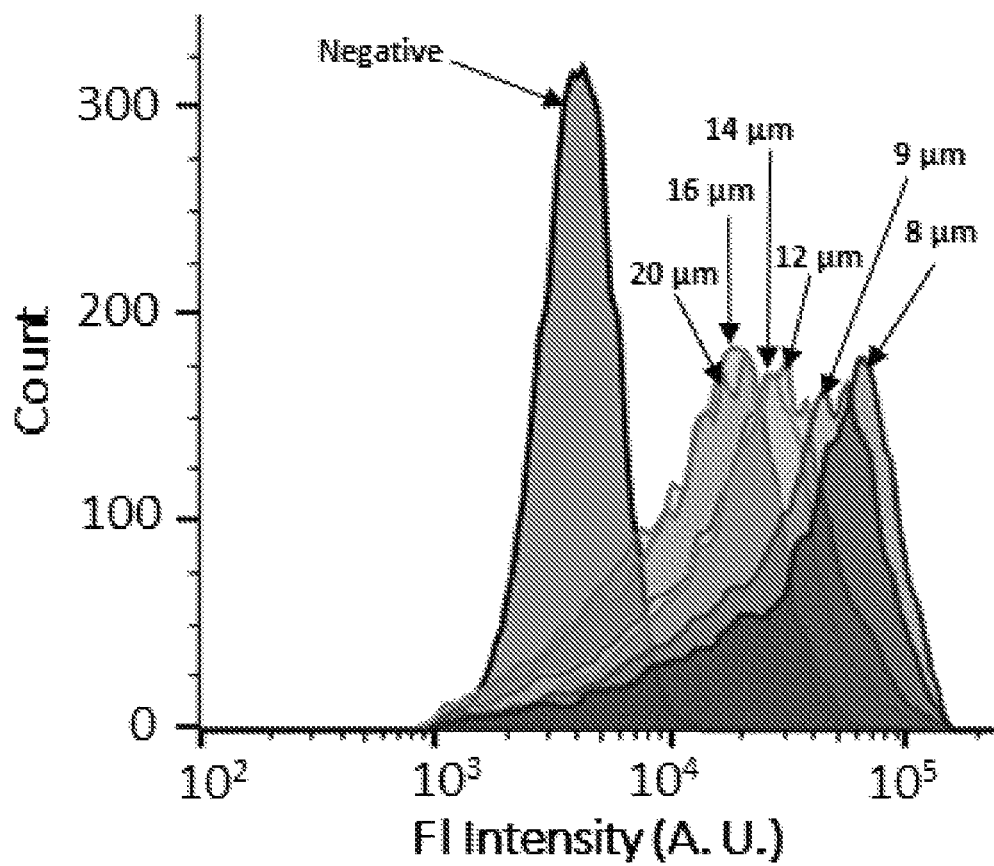
FIGS. 5a and 5b show various graphical representations indicating the intracellular molecular delivery increases with smaller compression gaps and faster flow conditions correspond to lower molecular delivery, respectively, in accordance with one or more embodiments of the present disclosure.
Figure 5B:
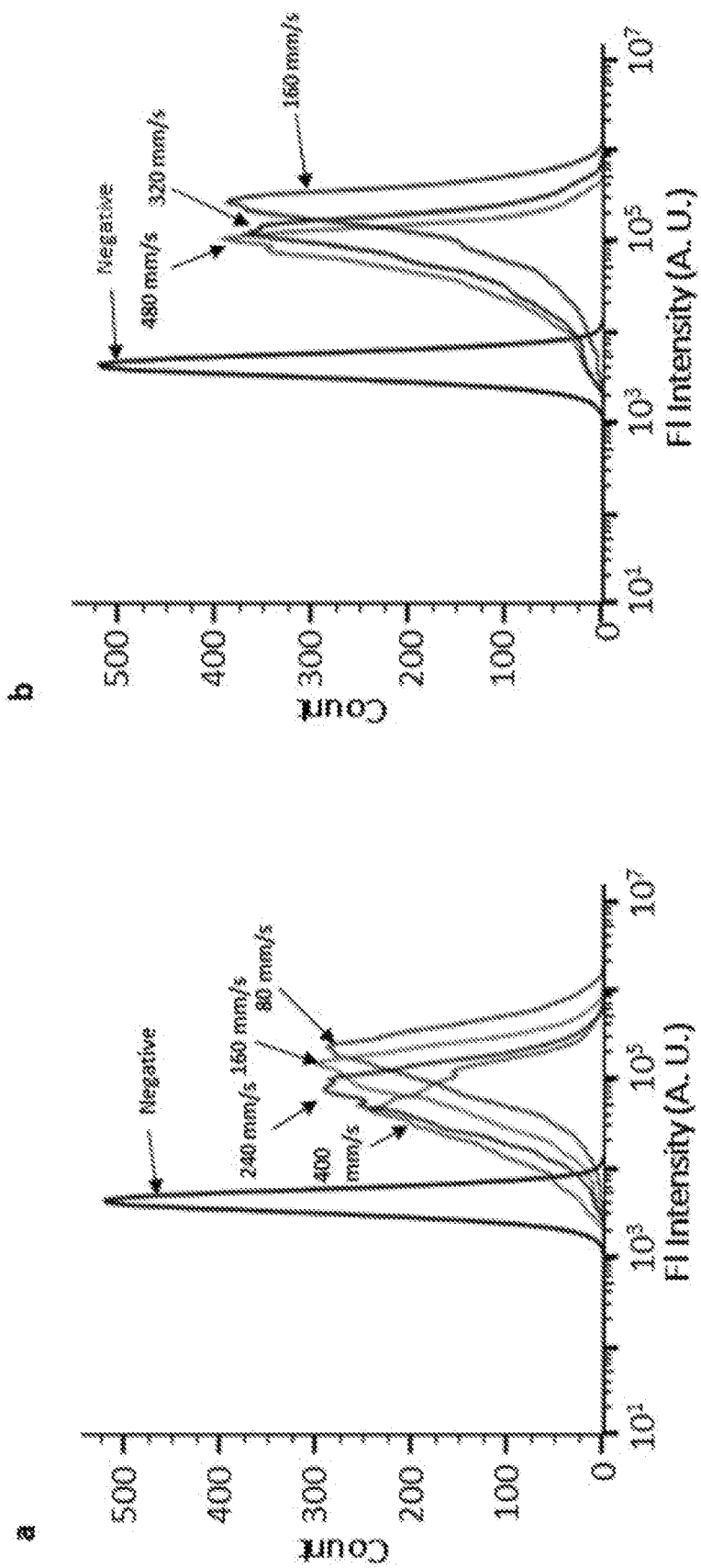

Confocal imaging determined that molecular delivery by the presently-disclosed systems and methods was dispersed throughout the cell interior, suggesting non-endocytic delivery (FIG. 4a). FIG. 4a shows confocal microscopy images of a single cell delivered with 2000 kDa TRITC-dextran with diffuse fluorescence profile throughout the cell interior. Scale bar is 5 µm. It was observed that greater compressions from smaller ridge gaps resulted in higher delivery of fluorescent molecules (FIG. 4b at (i) and FIG. 5a). FIG. 4b at (i) shows that molecule delivery increased with smaller size of ridge gap through which cells pass. FIG. 4b at (ii) shows that intracellular molecular delivery increases with smaller compression gap. Flow cytometry results determine the delivery of 2000 kDa FITC-dextran in K562 cells with devices of various ridge gap. Negative control cells were not exposed to FITC-dextran. The fluorescent signal showed a positive correlation with the measured volume loss associated with the gap size (FIG. 4b at (ii)). FIG. 4b at (ii) shows that molecule delivery was greater with increased volume change. K562 cells were processed in 7-ridge devices with 2000 kDa FITC-dextran. The measured delivery to cells with smaller gap dimensions (5.6 µm) was confounded at the conditions tested due to cells flowing around the ridges rather than passing through the smaller gap underneath the ridges. Ridges with gaps larger than the K562 cell diameter (14.5±1.5 µm) did not cause volume change, and showed lower delivery of 2000 kDa dextran macromolecules (FIG. 4b at (i)) in a manner consistent with existing studies that used fluid shear mechanoporation to induce membrane pores, allowing diffusive delivery of molecules.

Based on the correlation between volume loss and molecule delivery, it was hypothesized that altering the time that the cell relaxes as it moves between consecutive constrictions can affect the volume uptake and, therefore, molecular delivery. The relaxation time between ridges was controlled either by varying the ridge spacing or the flow rate. It was observed that that increased flow rate resulted in decreased delivery, while the 200 µm spacing between ridges consistently resulted in higher delivery than the 100 µm spacing (FIGS. 4b at (iii) and 5b). FIG. 4b at (iv) shows that Faster flow conditions correspond to lower molecular delivery. Flow cytometry results determine the delivery of 2000 kDa FITC-dextran in K562 cells at various flow rates with devices of (a) 100 µm ridge spacing and (b) 200 µm ridge spacing. Negative control cells were not exposed to FITC-dextran.

Therefore, the increased relaxation time between ridges led to greater delivery (FIG. 4b at (iv)), despite differences in flow speed and ridge spacing. It was also observed that molecular delivery showed diminishing returns past a certain duration of cell relaxation between ridges (~1 ms), suggesting a saturation point of relaxation (FIG. 4b at (iv)). As shown in FIG. 4b at (iv), the overall trend indicates delivery increased with greater cell relaxation time between the ridges until a plateau was observed. This result is in contrast with diffusive delivery, which increases with faster flow rates.

Characterization of Convective Molecular Delivery

Figures 6A, 6B:
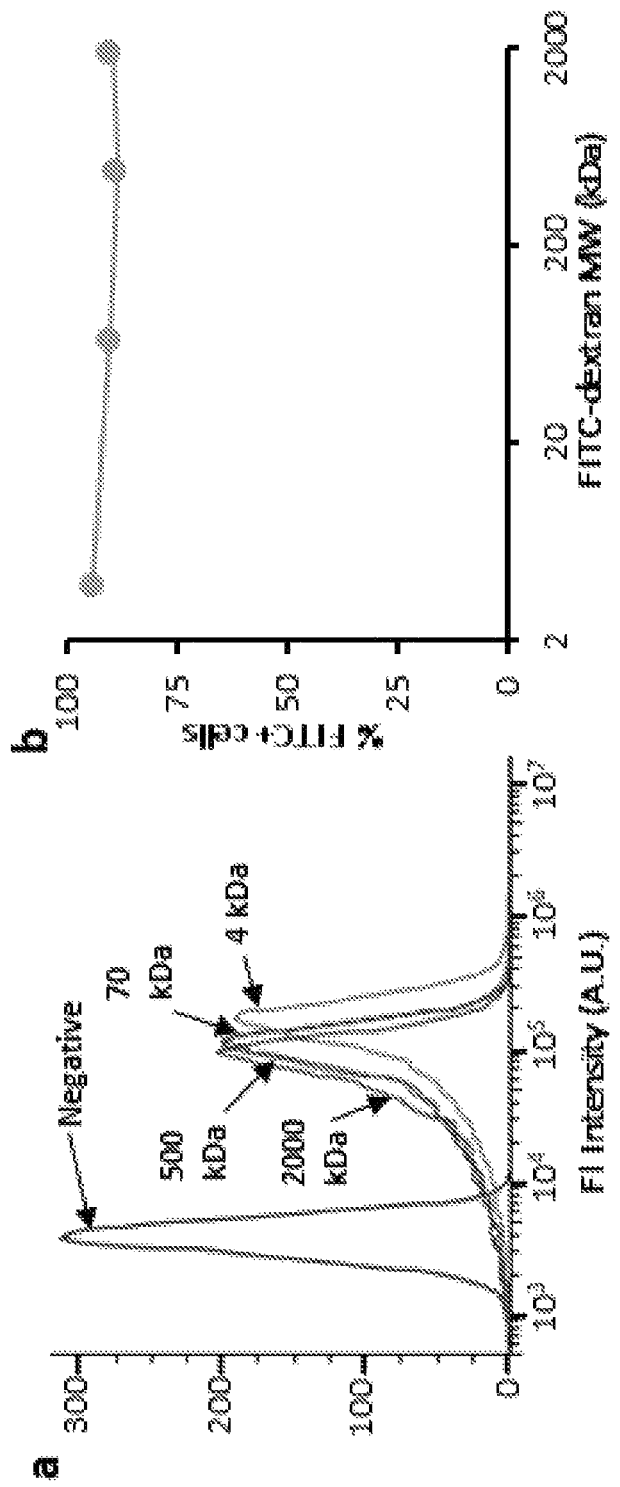
FIGS. 6a-6h are various graphical representations investigating various properties including molecule size, ridge count, and flow rate, in accordance with one or more embodiments of the present disclosure.

To further confirm that intracellular delivery occurs due to cell volume change, the methods were tested to see if they were affected by the size of the molecule. Since diffusion rate is inversely proportional to molecule size, diffusive delivery typically shows lower efficiency for larger macromolecules. In contrast, the described methods demonstrated intracellular delivery with high efficiency (~90% of cells uptake molecules) regardless of molecule size for the range tested (FIGS. 6a, 6b). This study used equal mass per volume of molecules ranging from 4 kDa, roughly the molecular weight (MW) of a small molecule drug, to 2000 kDa. This size-independent delivery supported the hypothesis that molecule uptake was achieved predominantly by advection of material from outside the cell due to cell volume recovery, rather than molecular diffusion through membrane pores.

Figures 6C, 6D:
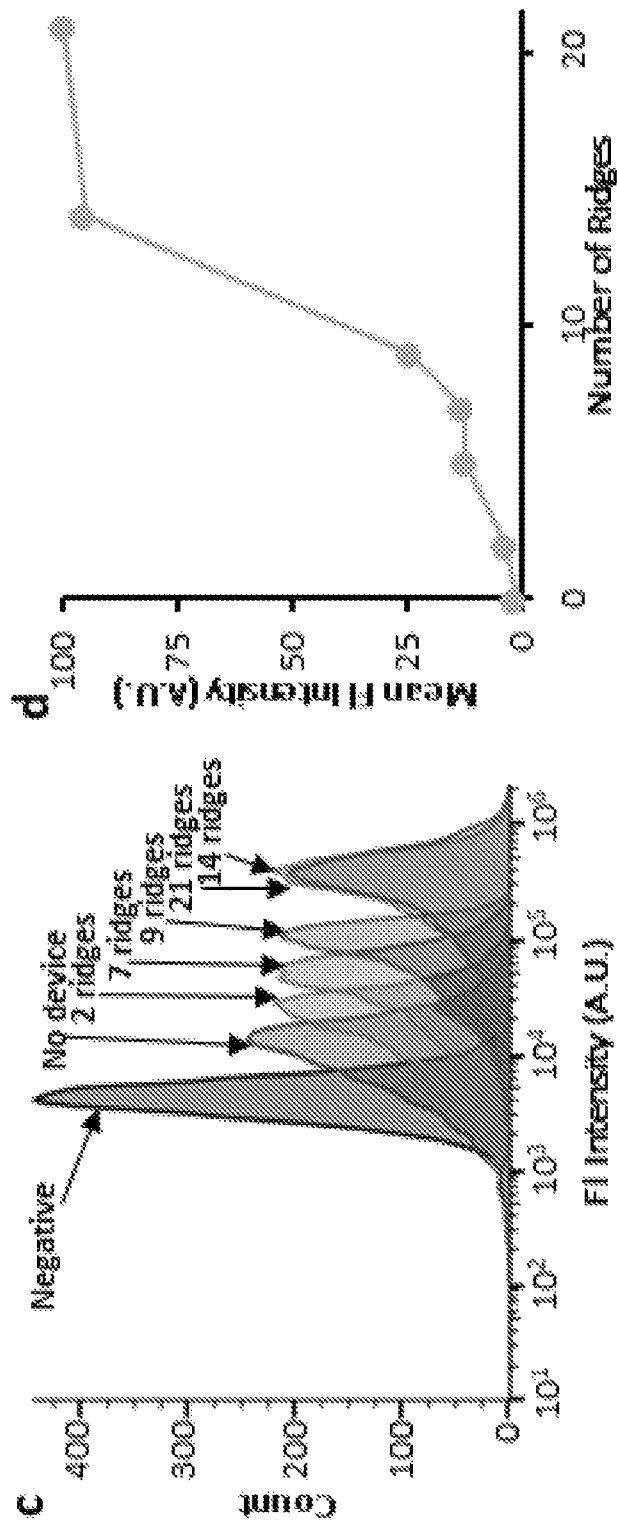
Figures 6E, 6F:
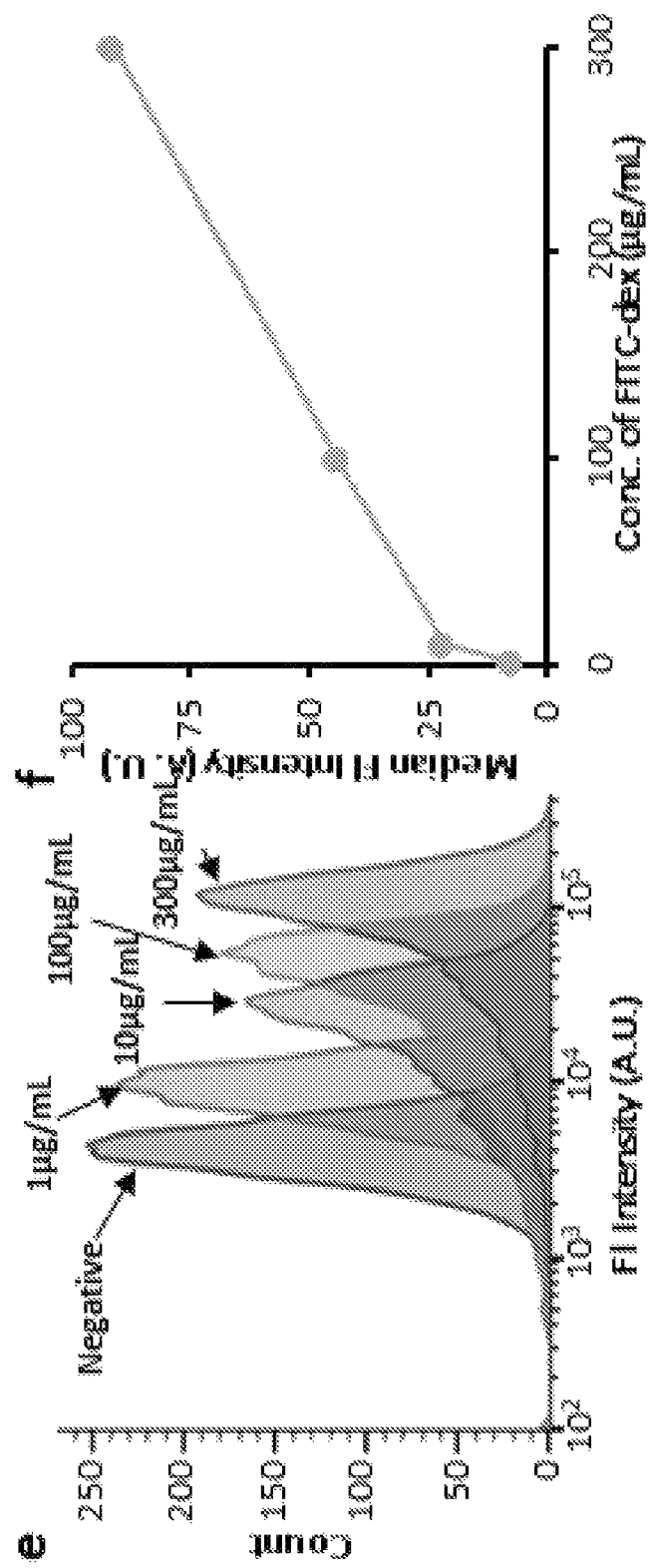

The use of multiple ridges greatly increased volume exchange and molecular delivery to the cells. A positive and non-linear correlation between the number of ridges and molecule delivery was observed, which saturated at 14 ridges for these experimental conditions (FIGS. 6c, 6d). The final molecular delivery was also found to be linearly dependent on the extracellular concentration (FIGS. 6e, 6f), indicating that saturation of the intracellular and extracellular molecule concentration was reached.

Figures 6G, 6H:
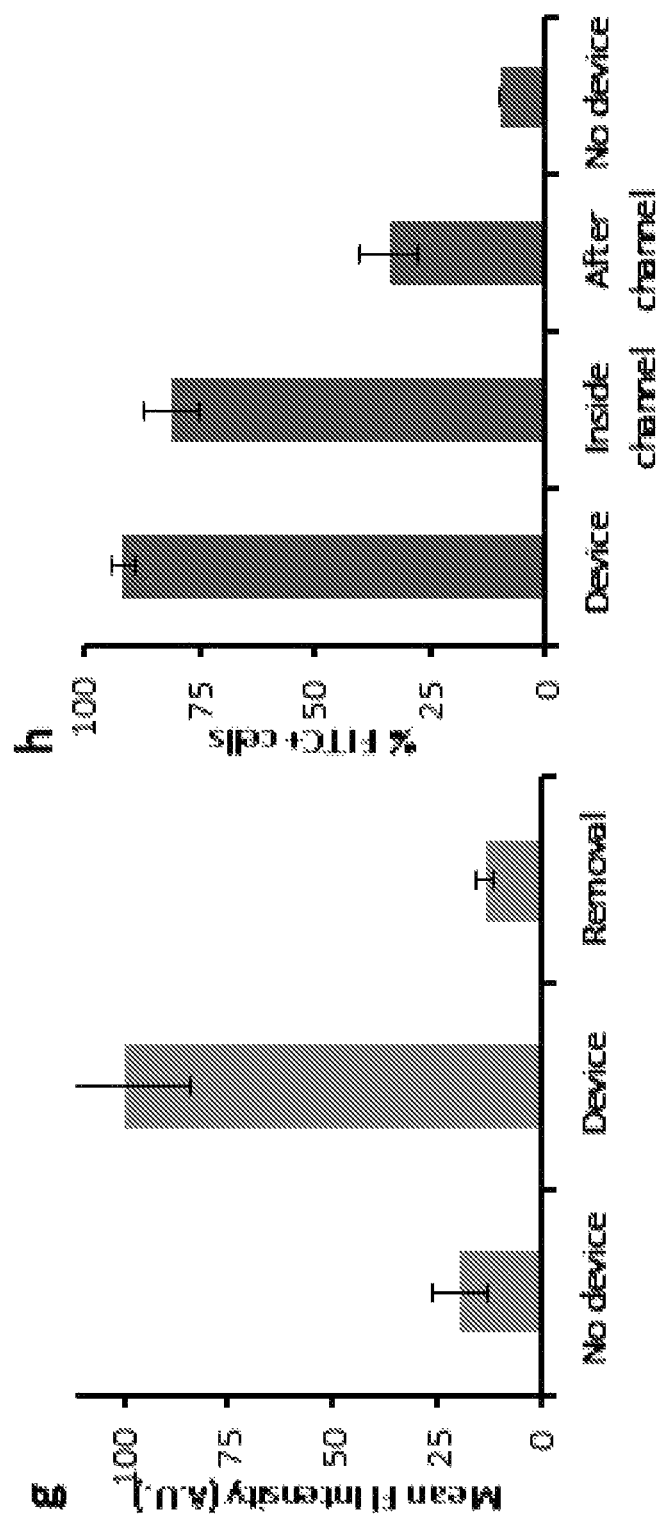

To further explore the hypothesis that the described systems and methods causes the cytosol to reach equilibrium with extracellular molecule concentration, the previously dextran-positive cells were processed with dextran-free buffer to remove the dextran from within the cells. 2000 kDa FITC-dextran was first delivered to K562 cells using the described systems and methods, then resuspending these delivered cells in FITC-free buffer and processed them in the device again for the Removal group. It was discovered that the Removal group had a mean fluorescence intensity that matches the No Device group, indicating that this method is highly effective in removing previously delivered molecules (FIG. 6g). These results support the assertion that the described systems and methods achieved molecule concentration equilibrium and can remove unbound molecules from the cell interior, a capability not demonstrated with diffusive delivery.

To determine the time scale at which delivery occurs during the described systems and methods, an experiment was designed to analyze the relative amount of delivery that occurs during the brief time (<0.1 s) of cell compressions inside the device channel and immediately after leaving the device. Delivery inside the channel was determined by flowing K562 cells through the channel with the target delivery molecules, 2000 kDa FITC-dextran, and then inhibiting delivery after the channel by immediately diluting the outlet sample into a molecule-free bath. Delivery after the channel was isolated by flowing cells through the channel in the absence of target molecules, then exposing the cells to a molecule-rich bath immediately after leaving the channel. Molecules were delivered to over 80% of cells during their <0.1 s transit through the channel, while only ~33% of cells exhibited delivery when provided dextran immediately after transit through the compressions, even after incubation in the outlet well for >10 minutes. A threshold of 10% of the No Device control was used to define the lower bound of fluorescence for positive delivery (FIG. 6h). The high delivery obtained primarily during compressions inside the channel supports that the described systems and methods deliver large macromolecules by fluid exchange during compression and relaxation.

Modeling Volume Exchange and Molecular Delivery

To better understand the relationship between volume change and intracellular delivery, a simple mathematical model of molecular delivery due to repeated volume exchange events was constructed. The model assumes the cell interior and exterior are well mixed and incompressible liquids. Therefore, as cells are compressed to volume VC under the ridge, a corresponding volume of liquid exits the cell carrying out a mass of target molecules dictated by the intracellular concentration of that species. Conversely, as a cell recovers lost volume, any species outside the cell are drawn in at a rate set by their external concentration and the time-dependent cell volume recovery V(t) (FIG. 7 at (a)). The cell fluorescence intensity is used to represent the amount of intracellular molecule delivery for the model and experimental results, with the assumption that cell fluorescence intensity is proportional to intracellular molecule concentration (FIG. 7 at (a))

Cell volume recovery was modeled after each compression as $V(t)=(V_c-V_0) \cdot e^{-t/\tau}+V_0$, where $V_0$ is the original (uncompressed) volume of the cell, $V_c$ is the cell volume under a ridge (which is assumed to be independent of ridge number), $\tau$ is the time for cells to recover ~66.7% of lost volume, and t is the amount of time that has passed after the most recent compression. The cell with volume $V_c$ is approximated to be a truncated sphere with height equal to the ridge gap. Based on the experimental results (FIG. 6h), it was assumed that the majority of delivery occurs immediately after compression, before the cell leaves the device. Therefore, delivery which occurs >1 ms after the last ridge was disregarded.

For the variable relaxation model, relaxation time $\tau(Z) = (\tau_0 - \tau_\infty) \cdot e^{-\zeta Z} + \tau_\infty$ is a function of the number of compressions (Z), the cell initial relaxation constant ($\tau_0$), and final relaxation constant ($\tau_\infty$) characterizing relaxation after many compressions. When fit to experimental data for molecule delivery, $\tau$ decreases with increasing number of ridges, as represented by the decay constant $\zeta$.

To calculate the amount of molecules delivered to a cell after a certain number of ridges, the contribution of each ridge was considered in order. The cell increase in volume between the first two ridges was men calculated as $[\Delta V]\_inc = V(t=t\_transit, z=0) - V\_c$, where t_transit is the time it takes the cell to travel between the two ridges, as calculated by the ridge spacing and fluid flow rate. The amount of molecules taken up by the cell between the two first ridges is then given as $[\Delta n]\_gain = C\_0 \cdot [\Delta V]\_inc$, where C0 is the external concentration of molecules. As the cell encounters the second ridge, it is compressed to Vc and some amount of molecules is forced out of the cell $[\Delta n]\_loss = n/V(t=t\_transit, z=0) \cdot [\Delta V]\_inc$ where n is the total amount of molecules in the cell at the current ridge. This procedure is then repeated for each subsequent ridge (while incrementing z) to determine the intracellular concentration after multiple compressions.

To allow comparison between the model and experimental data, values of $\tau_0$, $\tau_\infty$, and $\zeta$, were estimated by performing a nonlinear regression against the experimental data presented in FIG. 6d. Only the median fluorescence intensity values for each ridge (corrected using data from control cells which were never exposed to dextran or the presently disclosed systems and methods) were used to produce the fit. The predictions of the model were also compared to other datasets (while using the same parameters) by normalizing the experimental data and model predictions to their maximum values. Before normalization, experimental data for FIG. 7 at (c) was corrected using the same type of control used for the regression, and the experimental data for FIG. 7 at (d) were corrected using control cells exposed to dextran, but not run through the device.

A model was considered in which cells behave as a Kelvin-Voit viscoelastic material and expand after compression to exponentially to approach their original volume $V_0$. The asymptotic recovery was expressed using an exponential function $V(t) = (V_c - V_0) \cdot e^{-t/\tau} + V_0$ where t is the time elapsed after the most recent compression (FIG. 7 at (a)). Constant volume exchange was assumed per ridge, where the factor $\tau$, the time for cells to recover 66.7% of lost volume, is independent from the number of compressions. However, it was determined that the results from the molecule delivery experiments are inconsistent with constant volume exchange per ridge (FIG. 7 at (b)).

Figure 7:
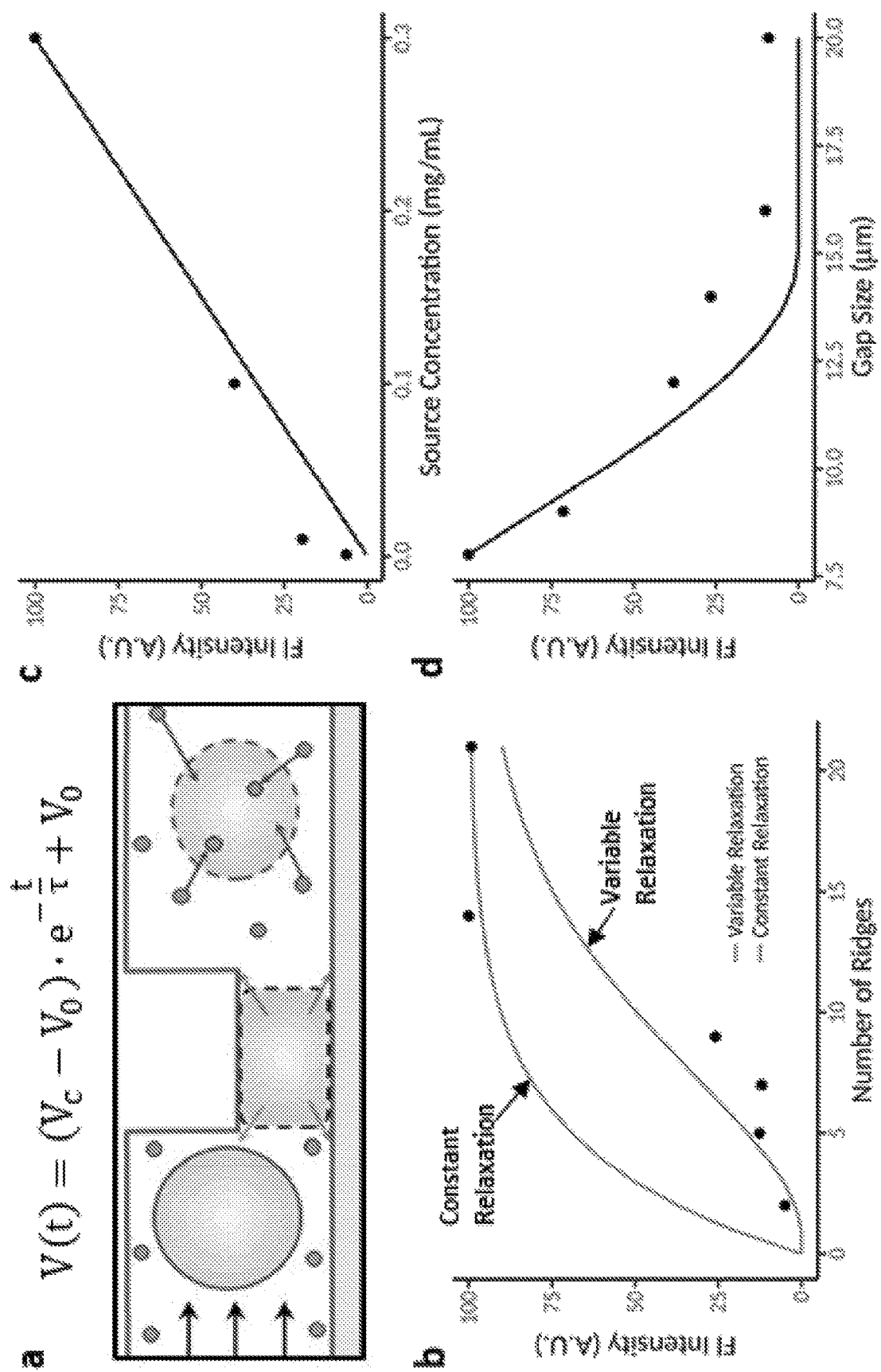
FIG. 7 shows development of a mechanistic model to incorporate cell volume exchange, in accordance with one or more embodiments of the present disclosure.

A model in which volume exchange increases with consecutive compressions (FIG. 7 at (b)) was considered next. It was assumed that relaxation time ($\tau$) decreases with repeated compressions, asymptotically approaching some final value. This model was then fitted to the experimental data, which yielded ($\tau$) that decreased from an initial value of ~1 s to ~0.1 ms after many ridges. Prior experiments suggest that relaxation of cells can indeed occur at time scales as slow as >10 s and as fast as ~10 µs with different compression conditions. The experimental results by the described systems and methods are consistent with the model of molecule delivery in which a nonlinear positive dependence is observed with increasing number of ridges, a linear dependence occurs with the source concentration, and a threshold gap size is needed for delivery (FIG. 7 at (b)-(d)).

Figure 8:
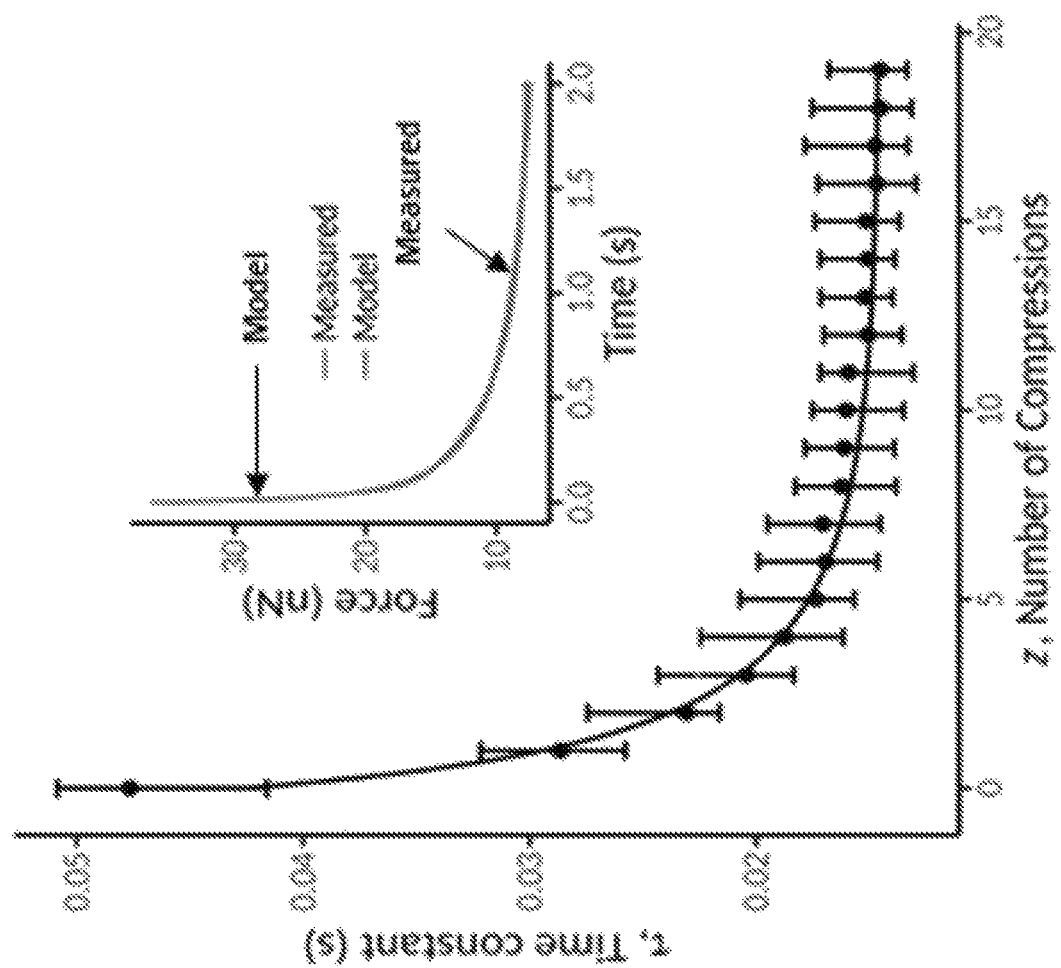
FIG. 8 is a graphical representation showing the effects of compression number on K562 cell relaxation time, in accordance with one or more embodiments of the present disclosure.

FIG. 7 at (b)-(d) show comparisons between the median fluorescence intensity observed in the experiments (dots) to the predictions of the model (solid lines). Using atomic force microscope (AFM) cell relaxation measurements, it was observed that cell shape recovery can indeed occur more rapidly after several compressions (FIG. 8). Based on this result and existing studies, it was hypothesized that repeated compressions by multiple ridges can lead to cell biophysical changes that result in faster cell deformation and recovery.

Applications of the Described Methods to Intracellular Delivery

Figure 9:
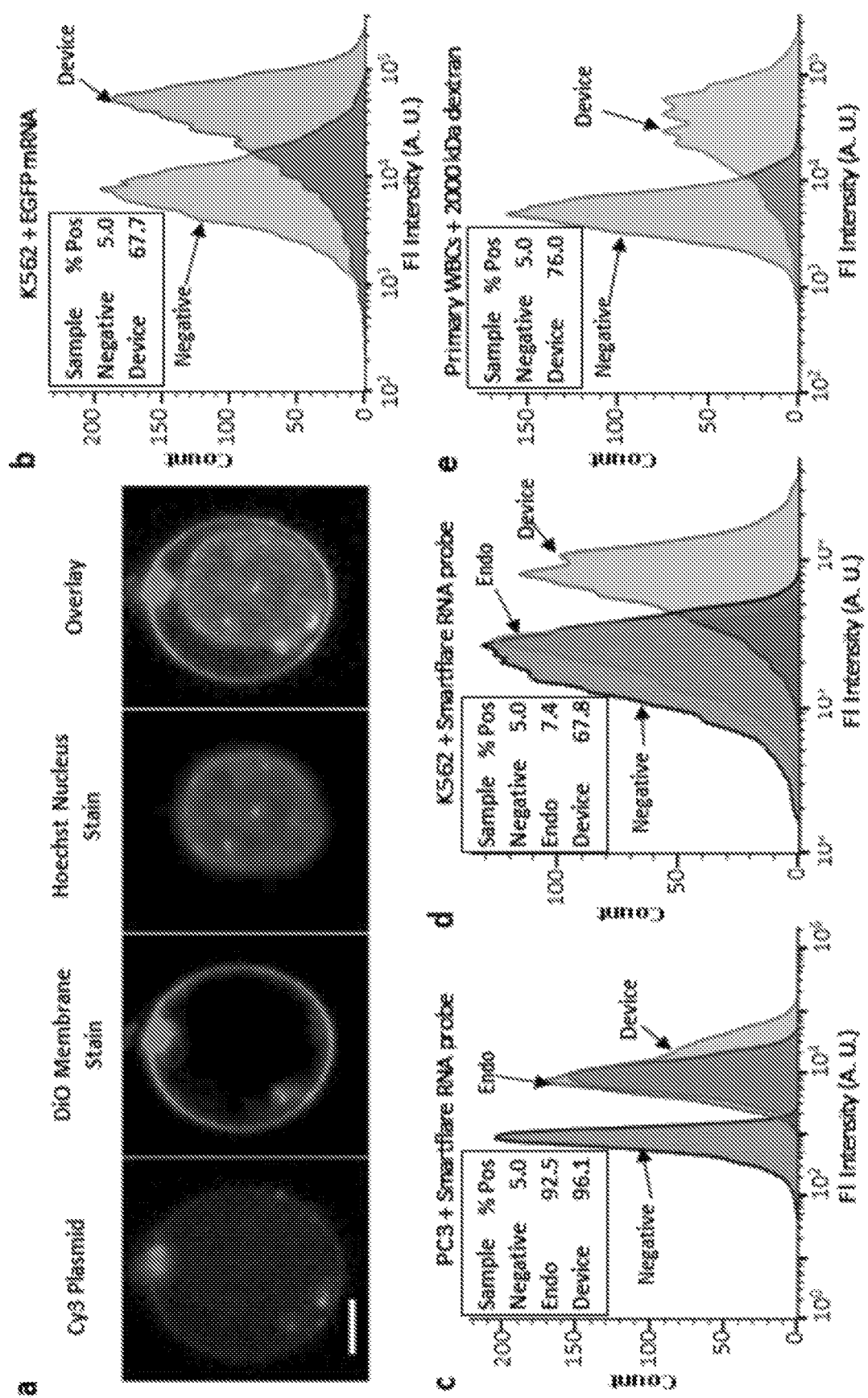
FIG. 9 shows various images and graphical representations showing successful delivery of a variety of molecules to cells, in accordance with one or more embodiments of the present disclosure.
Figure 10:
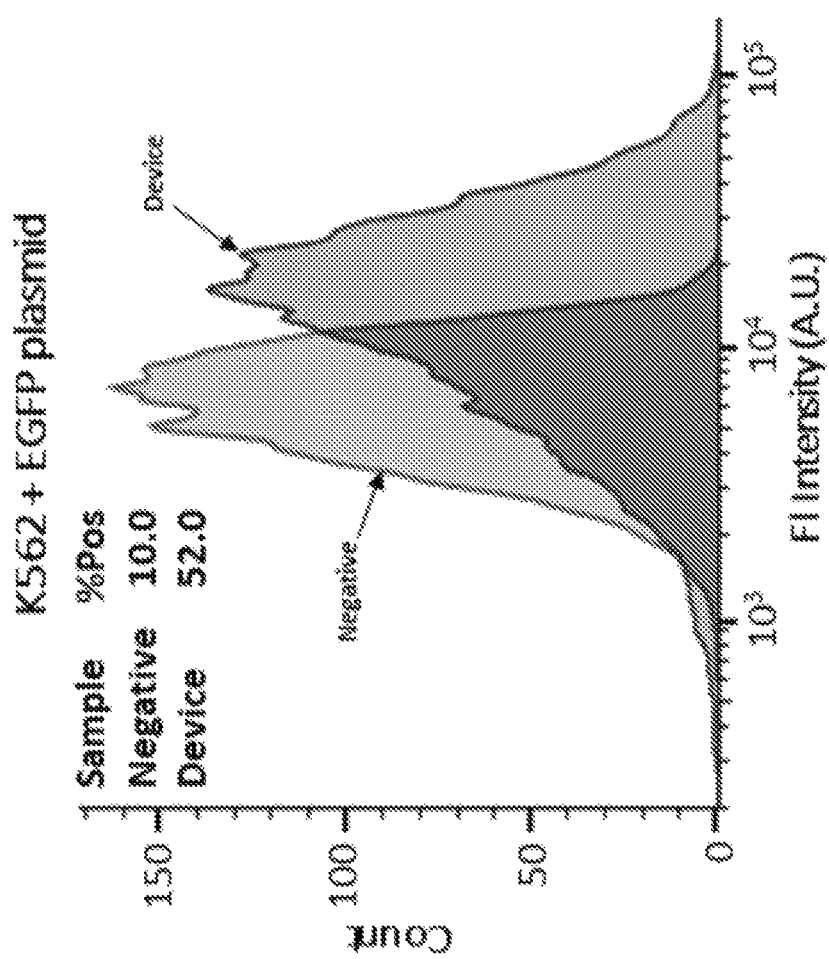
FIG. 10 shows flow cytometry results for the transfection of K562 cells using EGFP plasmid, in accordance with one or more embodiments of the present disclosure.

The application of the described systems and methods can address important limitations of microfluidic delivery platforms, particularly those that primarily use diffusive transport. To demonstrate the capabilities of the use of the described systems and methods as a highly efficient delivery platform for transfection agents, non-coding plasmids labeled with cyanine-3 (Mirus) into K562 cells were successfully delivered. The cells were stained with DiO membrane stain and Hoechst nucleus stain to visualize the intracellular localization of the Cy3-plasmids (FIG. 9 at (a)). Using confocal microscopy, the plasmid was shown to permeate the cell interior. Confocal microscopy showed diffuse delivery of Cy3-labeled plasmids throughout the interior of a cell with membrane and nucleus staining. Scale bar is 5 µm. A proof of concept transfection experiment successfully induced EGFP expression after delivery of EGFP mRNA (TriLink) and EGFP plasmid (OZ Biosciences) to K562 cells (FIGS. 9 at (b) and 10). FIG. 10 shows Flow cytometry results for the transfection K562 cells using EGFP plasmid. K562 cells were transfected using mechanovection alone with EGFP plasmid (OZ Biosciences). Negative control cells were not exposed to EGFP plasmid.

The described systems and methods were tested for potential applications for intracellular labeling and analysis by delivering SmartFlare Live Cell RNA probes (Millipore) to detect GAPDH RNA in K562 cells and adherent PC3 prostate cancer cells. Delivery to PC3 cells was competitive with the established method of 24 hr endocytosis, and was completed in less than 30 mins (FIG. 9 at (c)). Importantly, K562 cells, which do not uptake SmartFlare particles through endocytosis, showed successful delivery using the described systems and methods (FIG. 9 at (d)). The success in delivering to PC3 and K562 cells demonstrated this method's robustness for delivery to both adherent and nonadherent cells.

Figure 11:
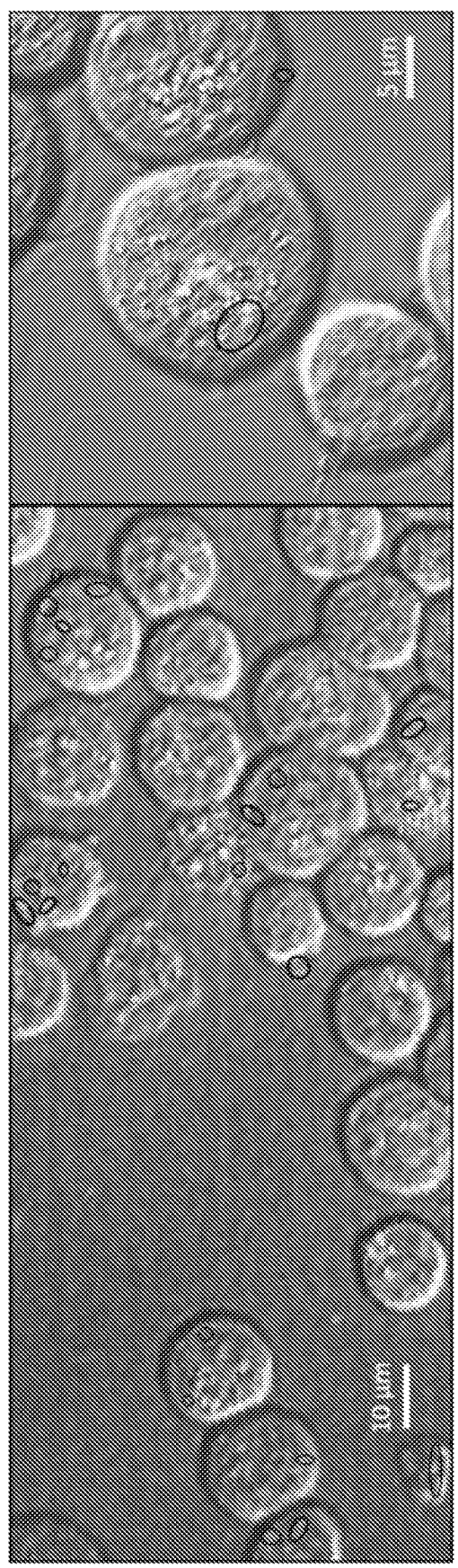
FIG. 11 shows confocal microscopy images of delivery of 100 nm fluorescent particles to K562 cells, in accordance with one or more embodiments of the present disclosure.
Figure 12:
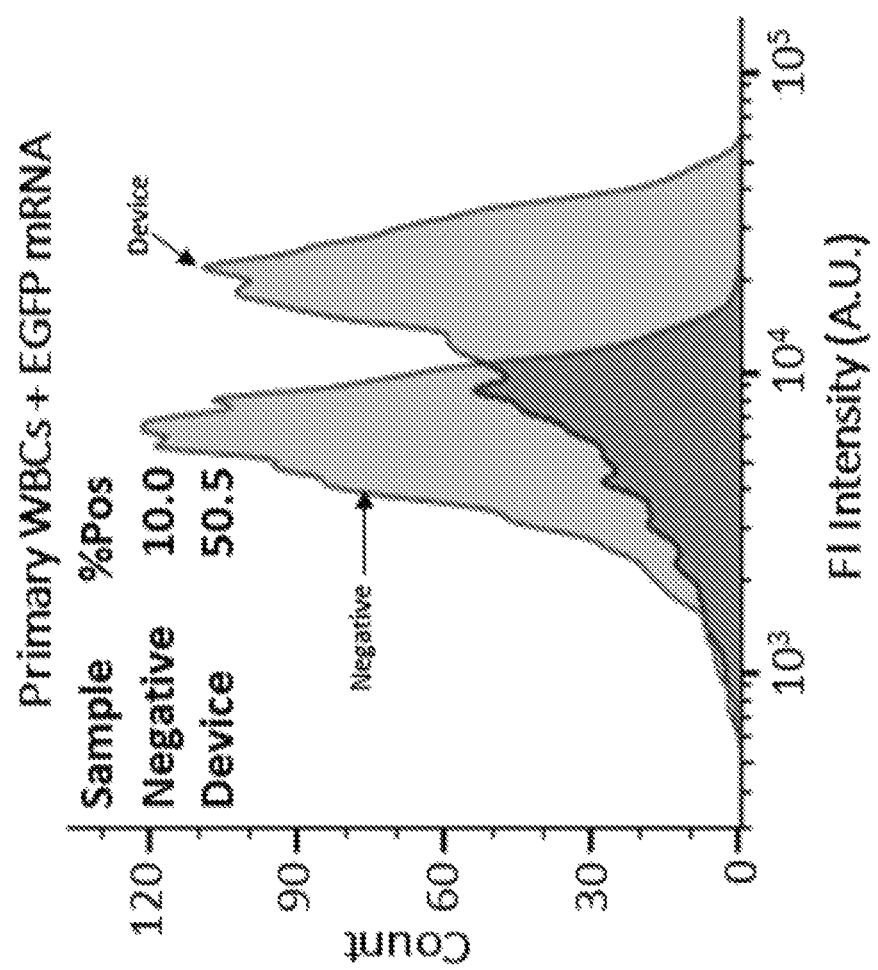
FIG. 12 is a graphical representation illustrating delivery of primary white blood cells and EGFP mRNA delivered to cells, in accordance with one or more embodiments of the present disclosure.

100 nm diameter fluorescent beads were also successfully delivered to K562 cells as a demonstration of this method's ability to deliver extremely large particles (FIG. 11). To address applications in cell engineering, the described systems and methods were used to transfect and deliver large macromolecules to primary peripheral blood mononuclear cells (PBMCs) isolated from whole blood (FIG. 9e and FIG. 12). FIG. 11 shows delivery of 100 nm fluorescent particles to K562 cells. Confocal microscopy shows fluorescent particles (red) delivered to the interior after microfluidic device processing. FIG. 12 shows flow cytometry results for the transfection of primary leukocytes isolated from donor blood using EGFP mRNA. Primary leukocytes were isolated from donor blood and transfected using mechanovection alone with EGFP mRNA (Trilink). Negative control cells were not exposed to EGFP mRNA. Furthermore, because the design of the angled ridges can avoid cell clogging, the processing using the described systems and methods was easily scaled up to multichannels to successfully process 50 million cells in 10 minutes without clogging. The demonstrated success in transfection and intracellular labeling for multiple cell types revealed the potential of this platform to compete with established delivery techniques for an array of cell engineering applications (Table 1).

| Cell Type | Average cell diameter, µm | Ridge gap for optimal test device type, µm | Delivery by rapid mechanical deformation |
|---|---|---|---|
| K562 | 15 | 9 | Dextran, RNA, DNA, SmartFlare, 100 nm nanoparticles |
| Jurkat | 15 | 8 | Dextran |
| PC3 | 15 | 9 | SmartFlare |
| Primary White blood cells | 10 | 6.7 | Dextran, RNA |

Discussion

By using microfluidics to precisely induce rapid, brief, large strain compressions, surprising phenomenon of temporary cell volume exchange that maintains cell integrity, viability, and function was elucidated. A behavior wherein cells initially undergo sudden volume loss followed by fast volume recovery was discovered. Additionally, it was discovered that induced volume change is greater for larger strains imposed through smaller constrictions. It was also found that increased volume exchange required multiple ridges spaced such that there was sufficient time for cells to recover lost volume between each ridge. This effect of volume change and relaxation was used as a new approach to deliver molecules to cells. Specifically, rapid compression-driven volume loss worked in conjunction with cell relaxation to convectively drive volume and molecules into the cell interior.

The physical cause of this surprising cell behavior can be explained by considering the relevant forces imposed on the cell by the ridges. The sudden inertial compression under a ridge with stepwise profile is equivalent to a high velocity (~1 m/s) vertical impact on the cell to disrupt the membrane in a manner akin to a droplet splatter upon a surface. The subsequent physical constriction of the cell under the ridge results in rapid transfer of momentum to the liquid of the cell interior to drive fluid volume out of the cell. The brief nature of this compression causes cells to relax on a rapid time scale to uptake volume after compression. The observed rapid recovery is consistent with rapid, poroelastic recovery behavior of the cytoplasm at short time scales (<0.5 s) after brief compression. The ability of the cytoskeleton to regulate cell volume and retain solutes could explain the minimal impact of the described systems and methods on cell viability despite the initial volume loss.

In the described studies, it was found that the described systems and methods utilize an advection-dominated molecular driving mechanism to efficiently deliver molecules of a wide range of sizes and structures for many cell types, while maintaining high viability. The microfluidic approach avoids many of the prohibitive drawbacks of detrimental changes to cell state associated with using chemical, viral, or electrical processing. The simplicity of use and successful delivery of an array of biologically relevant macromolecules to various cell types demonstrated great potential for a wide range of highly valuable biomedical applications.

CONCLUSIONS

In this study, a new cell behavior was discovered wherein multiple, rapid, high strain compressions caused cell volume change and relaxation without impacting cell viability. It was found that this volume exchange caused extracellular molecules to be convected into the cell interior. The described systems and methods enable new applications for microfluidic molecular delivery, including high-throughput delivery of large macromolecules and particles. The described systems and methods have elucidated a new cell phenomenon with great potential to serve as a nearly universal intracellular delivery platform for a variety of biotechnology applications.

Example 2

The described systems and methods were also shown to be distinct from current diffusive mechanoporation platforms, both in mechanism and capability. Diffusive microfluidic mechanoporation methods used gradual constrictions to impart shear stress on cells in a manner that facilitates smooth cell flow and thus slower deformation. The compression creates a shear force on the cell membrane leading to membrane poration and extracellular molecular diffusion into the cell interior. While diffusion is a universal transport mechanism, it imposes constraints on delivery due to the inverse relationship between diffusivity and molecule size. Indeed, diffusive approaches to microfluidic mechanoporation have shown limited efficiency in the delivery of large macromolecules.

A microchannel having a 10.2 micrometer compression gap was used to compare the presently described systems and methods with a diffusive delivery approach.

Figure 13A:
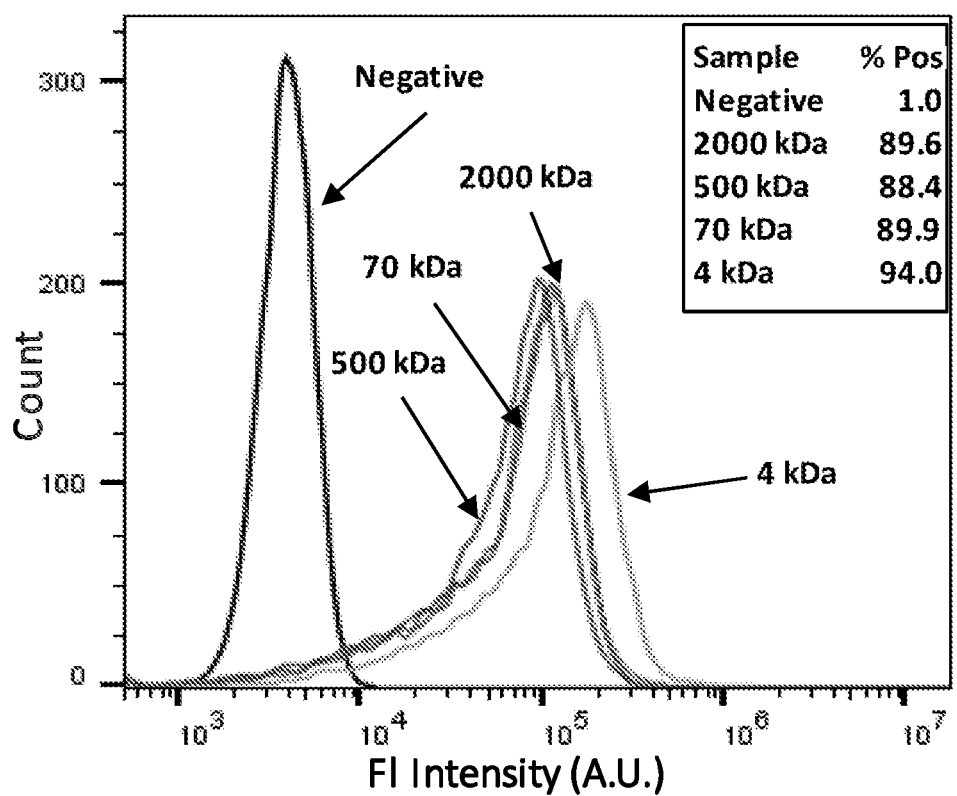
FIGS. 13a and 13b show graphical representations comparing intracellular delivery of various macromolecules of devices operating based on convective delivery (FIG. 13a) and diffusive delivery (FIG. 13b).
Figure 13B:
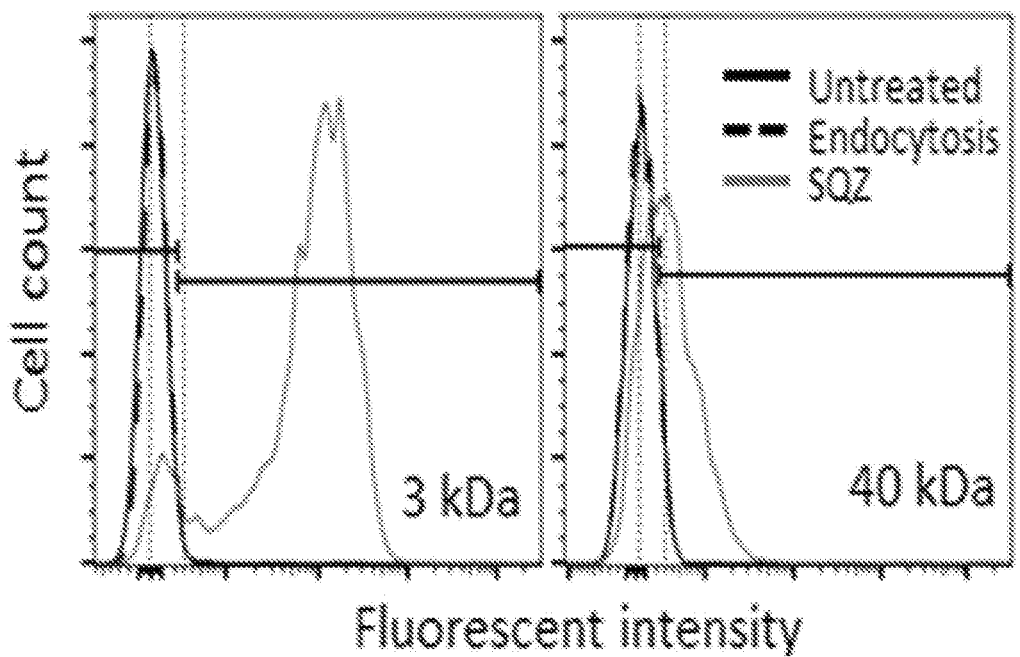
Figure 14A:
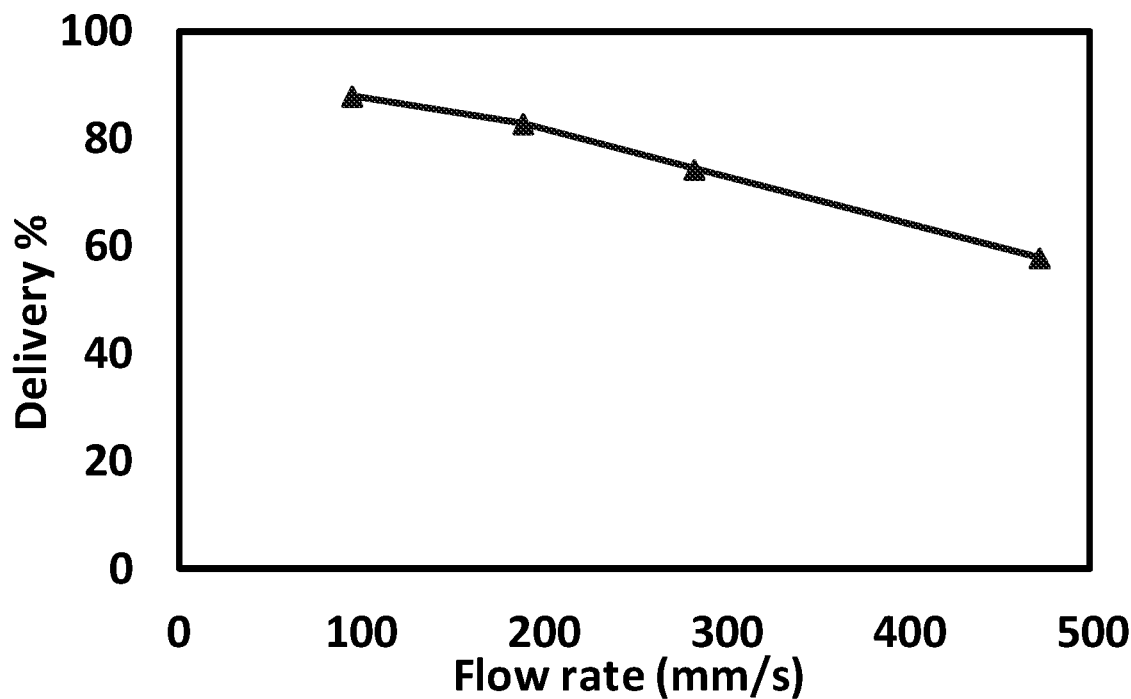
FIGS. 14a and 14b show graphical representations comparing flow rate and percent delivery in devices operating based on convective delivery (FIG. 14a) and diffusive delivery (FIG. 14b).
Figure 14B:
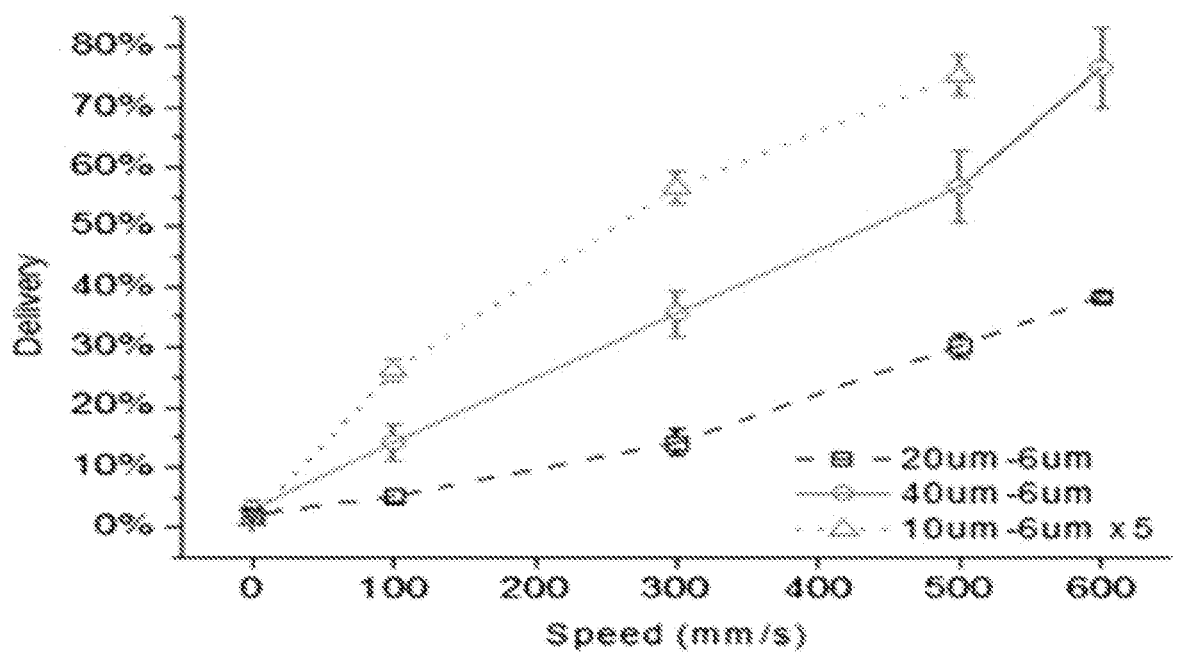
Figure 15A:
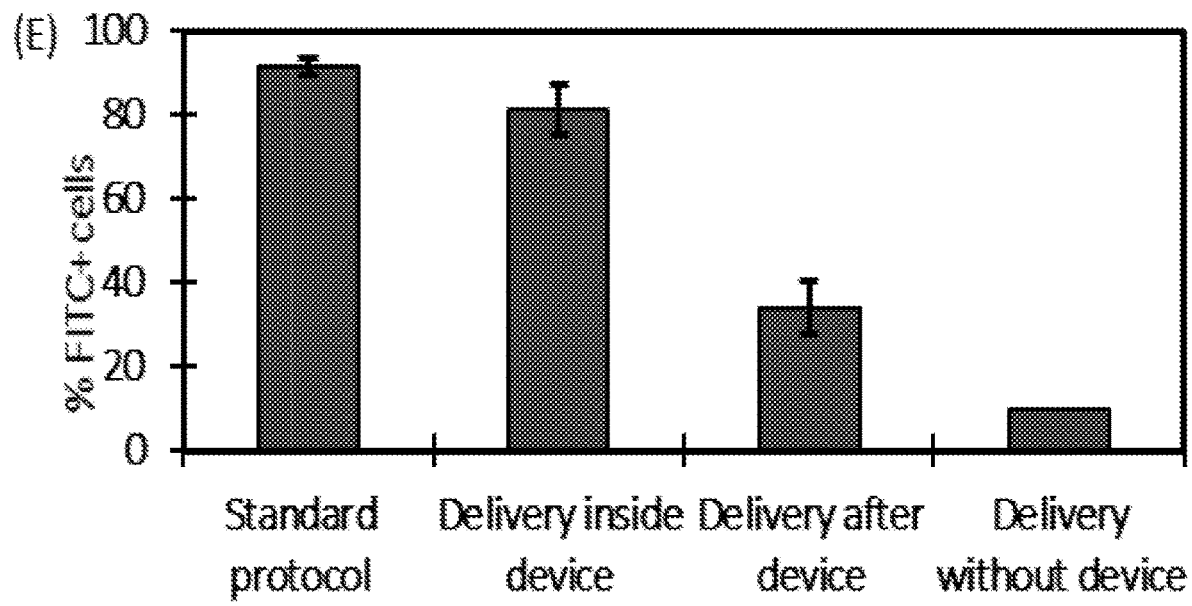
FIGS. 15a and 15b show graphical representations comparing intracellular delivery of macromolecules of devices operating based on convective delivery (FIG. 15a) and diffusive delivery (FIG. 15b).
Figure 15B:
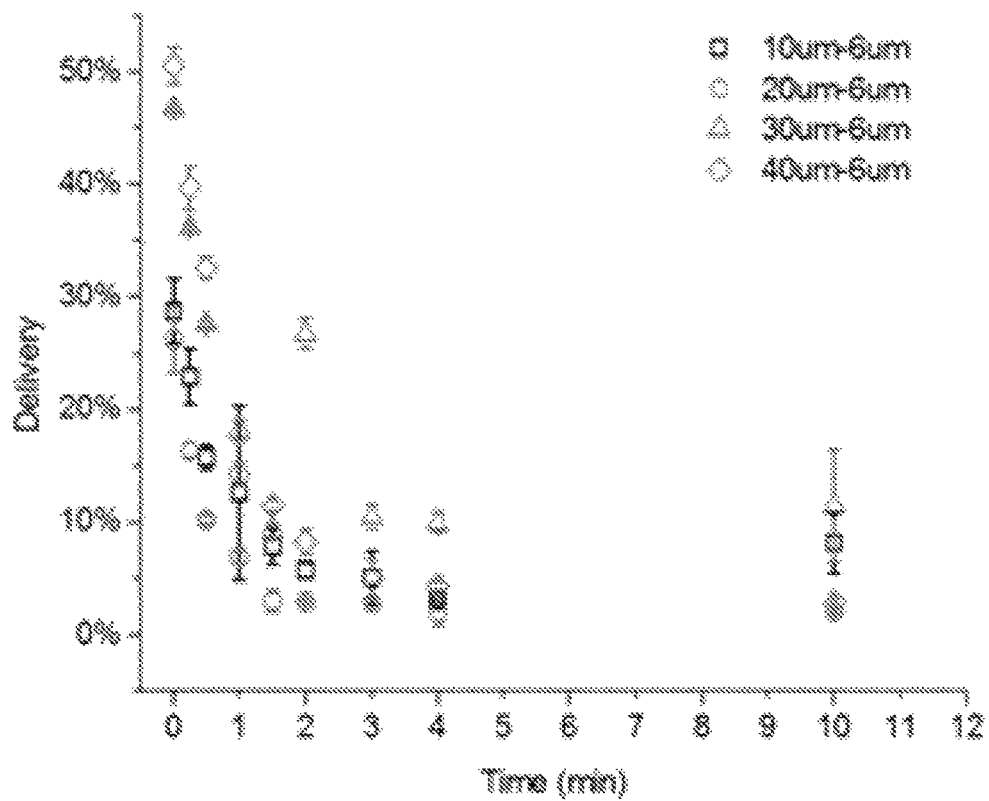

For instance, as illustrated in FIGS. 13a and 13b, a diffusive delivery approach (FIG. 13b) shows decreased delivery approach as the molecule size increased as compared to similar delivery for small and large molecules of the presently described systems and methods (FIG. 13a). Additionally, as illustrated in FIGS. 14a and 14b, high delivery was achieved using the presently described systems and methods (FIG. 14a) even with lower flow rate, as compared to a diffusion-based design which showed increased delivery as the flow rate increased (FIG. 14b). This is important because the diffusion-based design relies on shear forces, which at increased flow rates can result in cell destruction and cell death. Further, isolation of delivery that occurs inside the device demonstrated that 90% of standard protocol delivery can be achieved inside the device for the presently disclosed systems and methods (FIG. 15a) whereas in diffusion-based designs, delivery occurs after membrane disruption, as shown in FIG. 15b.

Figure 16A:
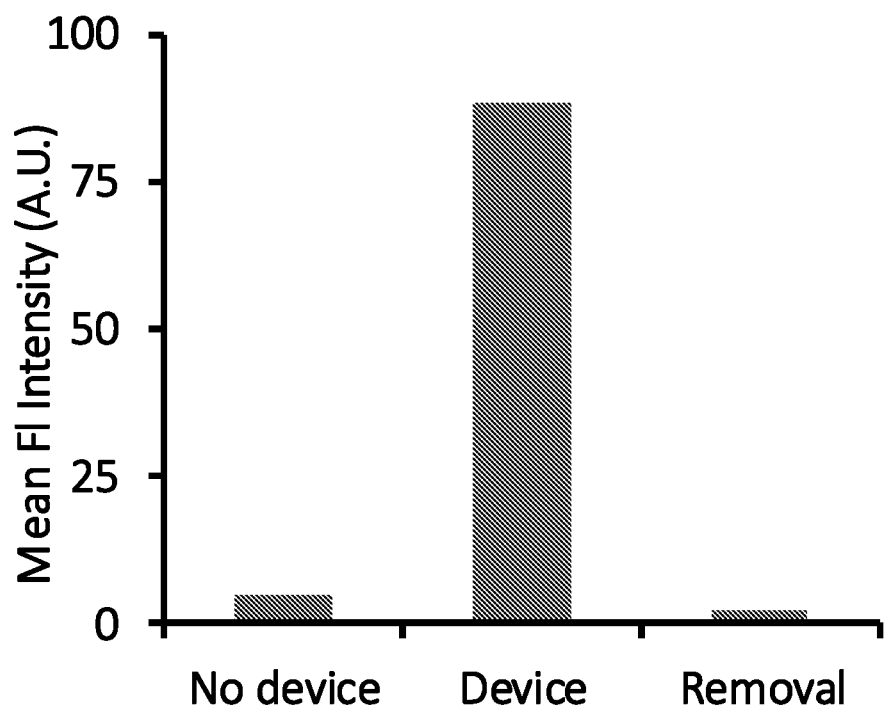
FIGS. 16a and 16b show graphical representations comparing intracellular delivery of dextran of devices operating based on convective delivery (FIG. 16a) and diffusive delivery (FIG. 16b).
Figure 16B:

Additionally, it was shown that the described systems and methods result in nearly complete homogenization attained by repeat volume exchange and complete removal, as shown in FIG. 16a. In contrast, the prior art devices relying on diffusion did not homogenize and resulted in incomplete removal, as shown in FIG. 16b. In these studies cells were delivered using standard delivery protocol and run once through a device with 0.3 mg/mL 2 MDa FITC-dextran. For removal, at least a portion of delivery cells were run through a new device one more time, this time without dextran. For the device/control, cells exposed to FITC-dextran without going through the device.

Further, the above-described systems and methods include improved clog prevention. Angled ridge design automatically and rapidly sorts out and removes large cell aggregates, non-viable cells, large cells, and non-processed cells.

While several possible embodiments are disclosed above, embodiments of the present disclosure are not so limited. These exemplary embodiments are not intended to be exhaustive or to unnecessarily limit the scope of the disclosure, but instead were chosen and described in order to explain the principles of the present disclosure so that others skilled in the art may practice the disclosure. Indeed, various modifications of the disclosure in addition to those described herein will become apparent to those skilled in the art from the foregoing description. Such modifications are intended to fall within the scope of the appended claims.

The embodiments of the present disclosure are also not limited to the particular formulations, process steps, and materials disclosed herein as such formulations, process steps, and materials may vary somewhat. Further, the terminology employed herein is used for the purpose of describing exemplary embodiments only and the terminology is not intended to be limiting since the scope of the various embodiments of the present disclosure will be limited only by the appended claims and equivalents thereof.

The specific configurations, choice of materials, and the size and shape of various elements can be varied according to particular design specifications or constraints requiring a device, system, or method constructed according to the principles of the disclosure. Such changes are intended to be embraced within the scope of the disclosure. The presently disclosed embodiments, therefore, are considered in all respects to be illustrative and not restrictive, and those skilled in the art will understand that variations and modifications can be effected within the scope of the disclosure as defined in the appended claims. The scope of the disclosure is therefore indicated by the following claims, rather than the foregoing description and above-discussed embodiments, and all changes that come within the meaning and range of equivalents thereof are intended to be embraced therein.

We claim:

1. A method for convective intracellular delivery comprising:
   providing a cell medium comprising a plurality of cells and a plurality of molecules to a microchannel, the microchannel comprising:
   a first wall, a second wall, and a plurality of ridges that are arranged in a chevron pattern oriented with respect to a central flow axis of the microchannel, the first and second walls being substantially planar to each other;
      wherein the plurality of ridges protrude outwardly from the first wall and define a plurality of compression gaps between the plurality of ridges and the second wall; and
      wherein the plurality of compression gaps have a height, measured perpendicular to the second wall, of from 20% to 80% of an average cell diameter of the plurality of cells; and
   a plurality of relaxation spaces disposed between the plurality of ridges;
   flowing the cell medium through the microchannel at a flow velocity, wherein as the cell medium flows through the microchannel, the plurality of cells undergo a convective intracellular delivery process comprising:
   compressing the plurality of cells in a first compression gap of the plurality of compression gaps, wherein the compressing causes the plurality of cells to undergo a loss in intracellular volume ($V_{loss}$); and
   passing the plurality of cells to a first relaxation space of the plurality of relaxation spaces, wherein the plurality of cells undergo a gain in volume ($V_{gain}$) and absorb a portion of the plurality of molecules from the cell medium; and
   collecting the plurality of cells in an outlet.

2. The method of claim 1, wherein a ridge angle formed by at least one ridge of the plurality of ridges is from 20 degrees to 90 degrees with respect to the central flow axis of the microchannel.

3. The method of claim 2, wherein the ridge angle is configured to affect trajectories of the plurality of cells within the microchannel.

4. The method of claim 2, wherein:
   the ridge angle is configured to facilitate movement of dead or damaged cells in the plurality of cells to a side wall of the microchannel thereby preventing clogging of the microchannel; and
   the side wall extends between the first wall and the second wall.

5. The method of claim 1, wherein a ridge angle formed by at least one ridge of the plurality of ridges is 30 degrees with respect to the central flow axis of the microchannel.

6. The method of claim 1, wherein a ridge angle formed by at least one ridge of the plurality of ridges is 45 degrees with respect to the central flow axis of the microchannel.

7. The method of claim 1, wherein the plurality of molecules are selected from the group consisting of macromolecules, nanoparticles, dextran, plasmids, mRNA, antibodies, beads, viruses, and combinations thereof.

8. The method of claim 7, wherein the plurality of molecules comprise macromolecules having an average size of from 3 kDa to 6 MDa.

9. The method of claim 1, wherein a width of at least one of the plurality of relaxation spaces is from 100 microns to 300 microns between two adjacent ones of the plurality of ridges.

10. The method of claim 1, wherein the plurality of are substantially orthogonal to to the first wall.

11. The method of claim 1, wherein the flow velocity is from 3 mm/sec to 500 mm/sec.

12. The method of claim 1, wherein the loss in intracellular volume ($V_{loss}$) is from 5% to 30% of an average cell volume of the plurality of cells.

13. The method of claim 1, wherein the loss in intracellular volume ($V_{loss}$) occurs in between 1 microsecond and 1000 milliseconds from when each cell of the plurality of cells first encounter one of the plurality of ridges.

14. The method of claim 1, wherein the gain in volume ($V_{gain}$) is from 25% to 100% of the loss in intracellular volume ($V_{loss}$).

15. The method of claim 1, wherein the gain in volume ($V_{gain}$) of at least 10% of the loss in intracellular volume ($V_{loss}$) occurs in from 4 microseconds to 100 microseconds.

16. The method of claim 1 further comprising, while flowing the cell medium through the microchannel, sorting the plurality of cells based on one or more of viscoelasticity, stiffness, elasticity, and adhesion.

17. The method of claim 1, wherein the convective intracellular delivery process further comprises:
   compressing the plurality of cells in a second compression gap of the plurality of compression gaps, wherein the compressing in the second compression gap causes the plurality of cells to undergo a second loss in intracellular volume ($V_{loss2}$); and passing the plurality of cells to a second relaxation space of the plurality of relaxation spaces, wherein the plurality of cells undergo a second gain in volume ($V_{gain2}$) and absorb a second portion of the plurality of molecules from the cell medium while in the second relaxation space.

18. The method of claim 17, wherein at least one of the gain in volume ($V_{gain}$) and the second gain in volume ($V_{gain2}$) is at least 10% of one of the loss in intracellular volume ($V_{loss}$) and the second loss in intracellular volume ($V_{loss2}$).

19. The method of claim 1, wherein the plurality of ridges comprise 5 ridges to 50 ridges, each ridge defining a separate one of the plurality of compression gaps.

20. The method of claim 1, wherein the plurality of compression gaps are configured to allow simultaneous passing of multiple cells of the plurality of cells through each of the plurality of compression gaps.

* * * * *